United States Patent [19]

Endo et al.

[11] 4,340,728

[45] Jul. 20, 1982

[54] NUCLEOSIDE DERIVATIVES AND PROCESS FOR PREPARING SAME

[75] Inventors: Takeshi Endo, Kamiichi; Katsumi Sakai, Jamiichi; Kiyoaki Chou, Kamiichi; Yoshitaka Inamoto, Namerikawa; Haruhiko Teshigawara, Kamiichi, all of Japan

[73] Assignee: Fuji Kagaku Kogyo Kabushiki Kaisha, Toyama, Japan

[21] Appl. No.: 210,796

[22] Filed: Nov. 26, 1980

[30] Foreign Application Priority Data

Nov. 28, 1979 [JP] Japan .................................. 54-152922
Dec. 27, 1979 [JP] Japan .................................. 54-169201

[51] Int. Cl.³ ...................... C07H 19/06; C07H 19/08
[52] U.S. Cl. ..................................................... 536/23
[58] Field of Search ................................ 536/23, 29; 260/112.5 R; 424/180

[56] References Cited

U.S. PATENT DOCUMENTS 3,155,646 11/1964 Hunter .................................. 536/23
3,407,191 10/1968 Gerzon .................................. 536/23
4,096,324 6/1978 Kelly et al. .......................... 536/29

*Primary Examiner*—Blondel Hazel
*Attorney, Agent, or Firm*—Birch, Stewart, Kolasch & Birch

[57] ABSTRACT

New nucleoside derivatives possessing strong anti-tumor activity with low toxicity, represented by the general formula:

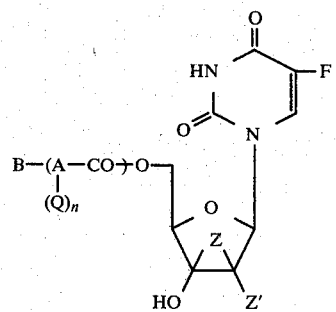

wherein $(A-CO-)$ is a residue of a saturated straight or branched chain fatty acid, B is a nitrogen-containing group, Q is a substituent of the fatty acid, Z and Z' each is H or OH with the proviso that both of Z and Z' are not OH, and n is zero or an integer of at least 1, as well as physiologically acceptable salts thereof. These nucleoside derivatives are prepared by introducing the nitrogen-containing acyl group directly in one step or indirectly in two steps into the 5'-position of 5-fluorouridine, 2'-deoxy-5-fluorouridine or 1-β-D-arabinofuranosyl-5-fluorouracil and splitting off any protective group and optionally converting the free compound into a physiologically acceptable salt thereof or vice versa.

7 Claims, No Drawings

NUCLEOSIDE DERIVATIVES AND PROCESS FOR PREPARING SAME

BACKGROUND OF THE INVENTION

1. Field of the Invention

The present invention relates to new nucleoside derivatives possessing anti-tumor activity and to processes for the preparation of such derivatives. More particularly, the present invention relates to new 5-fluorouridine, 2'-deoxy-5-fluorouridine and 1-β-D-arabinofuranosyl-5-fluorouracil derivatives carrying a nitrogen-containing acyl group in the 5'-position thereof and possessing strong anti-tumor activity in combination with low toxicity as well as processes for the preparation of such derivatives wherein the nitrogen-containing acyl group is introduced directly in one step or indirectly in two steps into the 5'-position of 5-fluorouridine, 2'-deoxy-5-fluorouridine or 1-β-D-arabinofuranosyl-5-fluorouracil.

2. Description of the Prior Art

5-Fluorouridine, 2'-deoxy-5-fluorouridine and 1-β-D-arabinofuranosyl-5-fluorouracil, which constitute the main skeletal structure of the new nucleoside derivatives of the present invention, are all known as nucleosides. These compounds are already known to have anti-tumor activity, anti-bacterial activity and the like pharmacological properties. In fact, studies on syntheses and pharmacological properties of these known compounds are reported and disclosed, for example, in British Pat. No. 1,080,491 and U.S. Pat. No. 2,885,396, Proceedings of the Society for Experimental Biology and Medicine 97, 470 (1958) and Physicians' Desk Reference 34, 1455 (1980). However, these compounds are ill-balanced between pharmacological properties and toxicity. If the anti-tumor activity alone is taken up among these pharmacological properties, these known compounds exhibit undesirably high toxicity at a level where the anti-tumor activity becomes effective. For these reasons, therefore, 2'-deoxy-5-fluorouridine alone is practically used as an anti-tumor agent only by way of a troublesome intrarterial injection because this compound is hardly absorbed merely by way of oral administration. Accordingly, a number of researches have been made on syntheses and anti-tumor activity of functional derivatives of these nucleosides for overcoming such disadvantages of the known nucleosides and discovering new pharmacologically effective derivatives thereof. A part of the researches is directed to synthesis and anti-tumor activity of esters of the nucleosides with fatty acids, and is disclosed, for example, in British Pat. No. 1,080,491, Biochemical Pharmacology 14, 1605 (1965), ibid. 15, 627 (1966), and Japanese Laid-open Patent Applns. Nos. 82079/70, 83378/70, 64280/75, 93983/75 and 133286/76. In all of these esters, however, the anti-tumor activity is not improved to a practically permissible extent. Another part of the researches is directed to synthesis and anti-tumor activity of esters of the nucleosides with phosphoric acid and its derivatives, and is disclosed, for example, in Proceedings of the Society for Experimental Biology and Medicine 104, 127 (1960), Cancer Research 22, 815 (1962), and Japanese Laid-open Patent Appln. No. 31677/78. The majority of these phosphoric esters are active forms of the nucleosides and are naturally supposed to be stronger in anti-tumor activity than the starting nucleosides. Actually, however, the anti-tumor activity of these esters does not reach a satisfactory level.

From the chemotherapeutic point of view, it is of importance that the synthesized derivatives of these nucleosides have to possess a high anti-tumor activity with a minimum level of toxicity. However, all the derivatives of the nucleosides synthesized hitherto are scarcely improved in anti-tumor activity so that if they are used in a dose sufficient enough to achieve the desired level of anti-tumor activity, their toxicity is concurrently increased to a practically impermissible extent.

Thus, there is still a great demand in this art for developing new derivatives of the nucleosides possessing a strong anti-tumor activity with a weak toxicity by chemically modifying the nucleosides in a simple manner.

BRIEF SUMMARY OF THE INVENTION

Accordingly, it is an object of the present invention to provide new nucleoside derivatives which are effective anti-tumor agents useful for both injection and oral administration.

It is another object of the present invention to provide new nucleoside derivatives which are strong in anti-tumor activity and possess good absorbability in the living body with very low toxicity.

It is still another object of the present invention to provide processes for the preparation of the new nucleoside derivatives wherein a nitrogen-containing acyl group is introduced in one or two steps into the 5'-position of the nucleosides in a simple manner.

It is a further object of the present invention to provide the use of the new nucleoside derivatives as anti-tumor agents.

Other objects, features and advantages of the present invention will become apparent more fully from the following description.

DETAILED DESCRIPTION OF THE INVENTION

With an attempt to synthesize new nucleoside derivatives possessing strong anti-tumor activity with extremely reduced toxicity, the present inventors have conducted research for esterifying the hydroxyl group in the 5'-position of the nucleosides with various carboxylic acids. As a result of the present inventors' extensive research, it has been found surprisingly that new nucleoside derivatives obtained by introducing a nitrogen-containing acyl group directly by esterification or indirectly in two steps by esterification followed by condensation into the 5'-position of the nucleosides exhibit strong anti-tumor activity with extremely reduced toxicity and good absorption even by oral administration. The present invention has been accomplished on the basis of the above finding.

In accordance with one embodiment of the present invention, there are provided new nucleoside derivatives of the general formula:

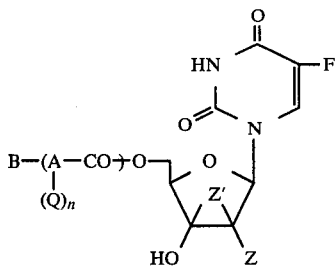

[I]

wherein (A—CO—) is a residue of a straight or branched chain fatty acid (i.e. a straight or branched chain alkylcarbonyl group), B is a nitrogen-containing group, Q is a substituent of the fatty acid, Z and Z' each is H or OH with the proviso that both of Z and Z' are not OH, and n is zero or an integer of at least 1, as well as physiologically acceptable salts thereof.

The acyl group (A—CO—) in the 5'-position carries 1-17 carbon atoms in the straight or branched chain alkyl moiety A and has the nitrogen-containing group B and optionally one or more substituents Q in the alkyl moiety. The nitrogen-containing group B is selected from a wide variety of inorganic and organic nitrogen-containing groups. Illustrative of the nitrogen-containing group B are, for example, substituted or unsubstituted amino groups bound in the α- or ω-position, such as an amino group ($H_2N-$), an acylamino group (RCONH—), an alkylamino group (R—NH—), hydroxylamino group (HONH—), nitrosoamino group (ONNH—), hydroxynitrosoamino group

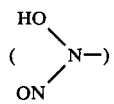

and hydroxyformylamino group

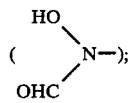

substituted or unsubstituted hydrazino groups such as a hydrazino group ($H_2NNH-$), an alkylhydrazino group (R—NHNH—) and a semicarbazido group (H NCONHNH—); substituted or unsubstituted guanidino groups such as a guanidino group

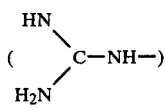

and an N-alkylguanidino group

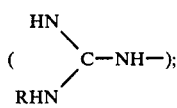

diazo group ($N_2=$); azido group ($N_3-$); nitro group ($O_2N-$); isocyano group (C≡N—); and 3–6 membered heterocyclic amino groups in which the ring carbon chain may be interrupted by one or more hetero atoms, such as an aziridino group (N—), azetidino group (N—), pyrrolidino group (N—), piperizino group (N—), piperazino group (HNN—), morpholino group (ON—), dixopiperazino group (HNN—), pyrrolino group (N—) and imidazolyl group (N—).

In case the nitrogen-containing group B is an amino group ($H_2N-$), this group may be combined together with the carbon atoms in the alkyl moiety A of the acyl group $$(A-\underset{\underset{O}{\|}}{C}-)$$

to form a ring. Examples of such cyclized acyl group include prolyl, azetidinocarbonyl and hydroxyprolyl groups.

In case the group B is an acylamino group (R—CONH—), the moiety R in the N-acyl group is as a rule selected from $C_{1-11}$ alkyls such as methyl, ethyl, butyl, nonyl and undecyl, $C_{2-11}$ alkenyls such as vinyl, tiglyl, decenyl and underenyl an alkoxy such as ethyoxy, an aralkoxy such as benzyloxy, an aryl such as phenyl, an aralkyl such as benzyl or phenethyl, a heterocyclic alkyl such as 3-pyridylmethyl, an aroylthioalkyl such as benzoylthioethyl, a carboxyalkyl such as 2-carboxyethyl, and substituted and unsubstituted amino such as amino, alkylamino and N-nitrosoalkylamino. Accordingly, preferable examples of the N-acyl group (R—CO—) include ethoxycarbonyl, benxyloxycarbonyl, an aroyl such as benzoyl, phenylalkanoyl such as phenylacetyl or phenylpropionyl, 3-pyridylacetyl, 2-benzoylthiopropionyl, an acyl group of substituted or unsubstituted dicarboxylic acids such as 3-methoxycarbonylpropionyl, 3-ethoxycarbonylpropionyl or succinyl, carbamoyl, N-alkylcarbamoyl, N-alkyl-N-nitrosocarbamoyl, an alkanoyl or alkenoyl with 1–11 carbon atoms such as acetyl, propionyl, tiglyl or decanoyl, and hydroxylalkanoyl such as lactyl or 2,3-dihydroxypropoxyacetyl.

The substituent Q which may be present in the alkyl moiety A of a residue of the saturated straight or branched chain fatty acid is selected from a hydroxyl group, mercapto group, an alkoxy group such as a methoxy group, an aralkoxy group such as a benzyl group, an alkylmercapto group such as a methylthio group, an aralkylthio group such as a benzylthio group, a substituted or unsubstituted carboxyl group such as carboxyl or an alkyloxycarbonyl, a substituted or unsubstituted an amino group such as amino group, alkylamino group or N-acylamino group, an aryl or ring-substituted aryl group such as a phenyl or hydroxyphenyl group, sulfinyl group, a heterocyclic group such as indolyl, imidazolyl or guanidyl group, and a dithio group (—S—S—) connected at one end to an amino acid such as

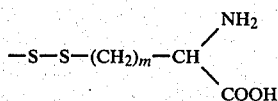

wherein m is an integer of at least 1. The majority of the substituents mentioned above with respect to Q are seen in amino acids of natural origin. The existence of the substituent Q is not indispensable in the nucleoside derivatives of the present invention. When n is 2, the two Q's may be different.

The grouping

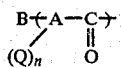

in the 5'-position as a combination of the residue of the saturated straight or branched chain fatty acid with the nitrogen-containing group B and the optional substituent Q results in principle from (a) natural or synthetic amino acids containing the unsubstituted free amino group or an amino group substituted by an acyl group or an alkyl group which may be fused to form a ring system and from (b) saturated fatty acids obtained in most of the cases by synthesis which carry the nitrogen-containing group B other than an amino group in the α- or ω-position. Illustrative of the amino acids (a) are, for example, those constituting proteins of living organisms, such as glycine, alanine, valine, leucine, isoleucine, serine, threonine, cysteine, methionine, aspartic acid, asparagine, glumatic acid, glutamine, arginine, lysine, hydroxylysine, histidine, phenylalanine, tyrosine, tryptophan, proline and 4-hydroxyproline; those not pertaining to the construction of proteins but playing an important role in living organisms, including amino acids other than α-amino acids, such as homocysteine, cysteinesulfinic acid, homoserine, ornithine, argininosuccinic acid, dopa, 3-monoiodotyrosine, 3,5-diiodotyrosine, thyroxine, α,γ-diaminobutyric acid, 2,3-diaminosuccinic acid, α-aminoadipic acid, α,β-diaminopropionic acid, saccharopine, β-alanine, γ-aminobutyric acid and β-aminobutyric acid; and those obtained by synthesis or biochemically produced by micro-organisms, such as acediasulfone, agaritine, alanosine, hadacidine, melphalan, ε-aminocaproic acid and ibotenic acid. Illustrative of the saturated fatty acids (b) containing the nitrogen-containing group B are, for example, morpholinopropionic acid and the like morpholinoalkanoic acids; azidopropionic acid and the like azidoalkanoic acids; hydrazino- or alkylhydrazinoalkanoic acids; nitroalkanoic acids; pyrrolidinoalkanoic acids; isocyanoalkanoic acids; guanidinoalkanoic acids; nitrosoamino acids; piperazinoalkanoic acids; and diazoalkanoic acids.

The nucleoside derivatives of the present invention possess strong anti-tumor activity usually with very weak toxicity. Illustrative of the typical nucleoside derivatives are 5'-O-(N-propylcarbamoylalanyl)-5-fluorouridine, 5'-O-(N-butylcarbamoylalanyl)-5-fluorouridine, 5'-O-(N-benzyloxycarbonylmethionyl)-5-fluorouridine, 5'-O-(N-decanoylmethionyl)-5-fluorouridine, 5'-O-{N-(3-phenylpropionyl)-methionyl}-5-fluorouridine, 5'-O-(N-pentanoylmethionyl)-5-fluorouridine, 5'-O-(N-benzyloxycarbonylprolyl)-5-fluorouridine, 5'-O-(N-benzyloxycarbonylvalyl)-5-fluorouridine, 5'-O-(N-butyrylvalyl)-5-fluorouridine, 5'-O-(N-propionylvalyl)-5-fluorouridine, 5'-O-(N-tiglylvalyl)-5-fluorouridine, 5'-O-(N-hexanoylvalyl)-5-fluorouridine, 5'-O-valyl-5-fluorouridine, 5'-O-(N-benzyloxycarbonylphenylalanyl)-5-fluorouridine, 5'-O-(N-pentanoyltyrosyl)-5-fluorouridine, 5'-O-azidoacetyl-5-fluorouridine, 5'-O-azidopropionyl-5-fluorouridine, 5'-O-(2- or 4-azidobutanoyl)-5-fluorouridine, 5'-O-(2- or 5-azidopentanoyl)-5-fluorouridine, 5'-O-(2-azidodecanoyl)-5-fluorouridine, 5'-O-(12-azidododecanoyl)-5-fluorouridine, 5'-O-(5-morpholinopentanoyl)-5-fluorouridine, 5'-O-{N-(2,3-dihydroxypropoxyacetyl)alanyl}-2'-deoxy-5-fluorouridine, 5'-O-(N-benzyloxycarbonylvalyl)-2-dexoy-5-fluorouridine, 5'-O-valyl-2-deoxy-5-fluorouridine, 5'-O-(2-morpholinopropionyl)-2-deoxy-5-fluorouridine, 1-{5'-O-(N-benzyloxycarbonylalanyl)-β-D-arbinofuranosyl}-5-fluorouracil, 1-{5'-O-(N-benzyloxycarbonylphenylalanyl)-β-D-arabinofuranosyl}-5-fluorouracil, 5'-O-(N-benzyloxycarbonylglycyl)-5-fluorouridine, 5'-O-(N-benzoyl- or N-pentanoyl- or N-decanoylglycyl)-5-fluorouridine, 5'-O-{N-(2-benzoylthiopropionyl)-glycyl}-fluorouridine, 5'-O-(N-benzyloxycarbonyl- or N-butyryl- or N-pentanoylalanyl)-5-fluorouridine, 5'-O-(N-propionyl- or N-succinyl- or N-phenylacetylmethionyl)-5-fluorouridine, 5'-O-(N-ethoxycarbonyl- or N-acetyl- or N-pentanoylvalyl)-5-fluorouridine, 5'-O-(N-propionyl- or N-pentanoylphenylalanyl)-5-fluorouridine, 5'-O-(N-propionyltyrosyl)-5-fluorouridine, 5'-O-(N-benzyloxycarbonyl-S-benzylcysteinyl)-5-fluorouridine, 5'-O-(N-benzyloxycarbonyltryptophanyl)-5-fluorouridine, 5'-O-N-benzyloxycarbonylseryl)-5-fluorouridine, 5'-O-(morpholinoacetyl or 2-morpholinopropionyl)-5-fluorouridine, 5'-O-(N-benzyloxycarbonyl- or N-lactoylalanyl)-5-fluorouridine, 5'-O-(N-butyryl-β-alanyl)-5-fluorouridine, 5'-O-(N-benzyloxycarbonylphenylalanyl)-5-fluorouridine, 5'-O-phenylalanyl-5-fluorouridine, 5'-O-(N-propionylphenylalanyl-5-fluorouridine, 5'-O-(N-propionyltyrosyl)-5-fluorouridine, 5'-O-(N-antanoyl-α-glutamyl)-5-fluorouridine, 5'-O-(N$^\alpha$-butyryllysyl)-5-fluorouridine and 5'-O-(N$^\omega$-benzyloxycarbonyl-N$^\alpha$-butyryllysyl)-5-fluorouridine.

As the new nucleoside derivatives of this invention contain one or more basic nitrogen atoms, they form acid addition salts with acids, particularly strong mineral acids. In this case, the acids are so chosen that the resultant acid addition salts are physiologically acceptable. Preferable acids for the acid addition salts include hydrochloric acid, hydrobromic acid, sulfuric acid and nitric acid. A strong organic acid such as citric acid may also be used, so far as it is chemically inert to the functional group of the nucleoside derivatives.

In accordance with the present invention, there is also provided a process for the preparation of the new nucleoside derivatives.

In one embodiment of the process, new nucleoside derivatives of the general formula:

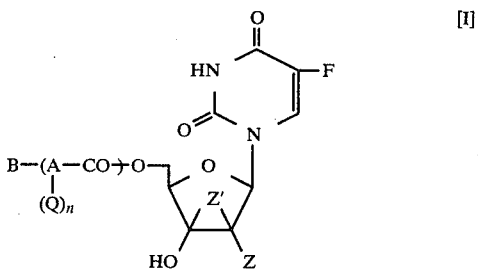

[I]

wherein (A—CO— is a residue of a saturated straight or branched chain fatty acid, A is a straight or branched chain alkyl moiety of the fatty acid, B is a nitrogen-containing group, Q is a substituent of the fatty acid, Z and Z' each is H or OH with the proviso that both of Z and Z' are not OH, and n is zero or an integer of at least 1 as well as physiologically acceptable salts thereof are prepared by subjecting a nucleoside of the general formula:

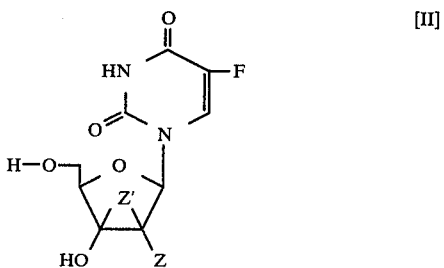

[II]

wherein Z and Z' have the same meanings as given above, to an esterification reaction with a saturated fatty acid of the general formula:

[III]

wherein A, B, Q and n have the same meanings as given above, splitting off any protective group from the resultant ester, and if desired, converting the free compound thus obtained into a physiologically acceptable salt thereof or vice versa.

In the above esterification reaction, the fatty acid of the general formula (III) is used usually in the form of a reactive functional derivative thereof such as an acid halide or an acid anhydride or mixed acid anhydride. The majority of the fatty acids of the general formula (III) are known and easily available in the market. However, these fatty acids including those not disclosed in literature can easily be prepared according to a method known per se.

The nucleoside of the general formula (II), i.e. 5-fluorouridine, 2'-deoxy-5-fluorouridine and 1-β-D-arabinofuranosyl-5-fluorouracil, are all known and are easily commercially available. This compound may be employed for the reaction as such. In such case, the esterification reaction takes place also at the hydroxyl groups in positions other than the 5'-position, thus resulting in the formation of a mixture of esters. In order to prevent a troublesome separation treatment of the desired product from the similar ester mixture and to perform the esterification reaction in high efficiency, all the hydroxy groups other than in the 5'-position are blocked with a protective group prior to the esterification reaction. The protection of hydroxy groups in positions other than the 5'-position can rather be said to be necessary for obtaining the desired 5'-ester alone selectively and at the same time preventing side reactions. Protective groups that can be used for this purpose are those where the group may be split off easily after the esterification reaction. Illustrative of such protective group are, for example, isopropylidene, ethoxyethylidene, benzylidene and benzyl groups. These protective groups can readily be split off by hydrolysis or hydrogenolysis according to methods known per se.

In general, the above esterification reaction is carried out in a usual manner by reacting a nucleoside of the general formula (II) with a saturated fatty acid of the general formula (III) in an anhydrous solvent in the presence of a basic substance as acid-binding agent and a condensing agent. If the fatty acid is used in the form of a reactive functional derivative thereof, for example, an acid halide thereof, the use of the condensing agent is omitted. An anhydrous aprotic solvent is used as a solvent in this reaction. Examples of such aprotic solvent include aromatic hydrocarbons such as benzene, toluene and xylene; halogenated hydrocarbons such as dichloromethane, chloroform, monochloroethane, dichloroethane and trichloroethane; ethers such as diethyl ether, tetrahydrofuran and dioxane; pyridine and nitromethane.

Illustrative of the basic substance are, for example, organic tertiary amines such as a trialkylamine, pyridine, picoline, lutidine and collidine; a tetraalkylammonium hydroxide; and inorganic bases such as sodium hydrogen carbonate, sodium carbonate, potassium carbonate and barium carbonate. The use of pyridine in an excess amount is advantageous in that pyridine exhibits a dual function as an aprotic reaction solvent and a basic substance for capturing an acid.

Preferred examples of the condensing agent include an arylsulfonyl halide such as p-toluenesulfonyl chloride and triisopropylbenzenesulfonyl chloride; an alkylsulfonyl halide such as methanesulfonyl chloride; an inorganic halide such as thionyl chloride or phosphorus oxychloride; and dicyclohexylcarbodiimide.

In this esterification reaction, an equimolar proportion of the reactants is required theoretically. However, the fatty acid, the basic substance and the condensing agent, if any, may be used in excess to increase the reaction rate of the nucleoside as the main starting material. Usually, about 1-3 molar proportion of the fatty acid of the general formula (III), the basic substance and the condensing agent, if any, can be used without influencing the reaction per mol of the nucleoside.

The reaction is conveniently carried out at room temperature. In general, the occurrence of side reactions can be inhibited at a lower temperature. Accordingly, the reaction mixture is cooled in certain cases to inhibit occurrence of such side reactions and at the same time to increase the yield of the end product. When the fatty acid of the general formula (III) is used in the form of a mixed acid anhydride, however, heating of the reaction mixture is required in some cases.

Usually, a period of 1-44 hours is required for completion of the esterification reaction.

In another embodiment of the process, the new nucleoside derivatives of the general formula (I):

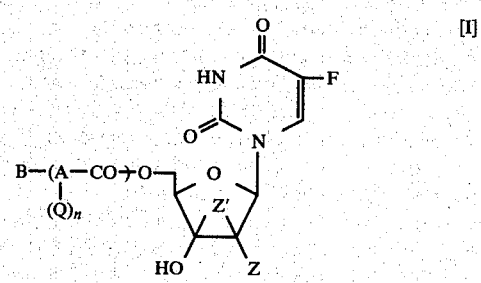

wherein A, B, Q, Z, Z' and n have the same meanings as given above, as well as physiologically acceptable salts thereof can be prepared by subjecting the nucleoside of the general formula (II):

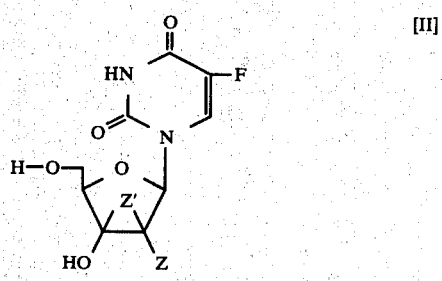

wherein Z and Z' have the same meanings as given above, to an esterification reaction with a saturated straight or branched chain fatty acid of the general formula:

wherein A, Q and n have the same meanings as given above and X stands for a radical replaceable with the nitrogen-containing group B, condensing the resultant ester of the general formula:

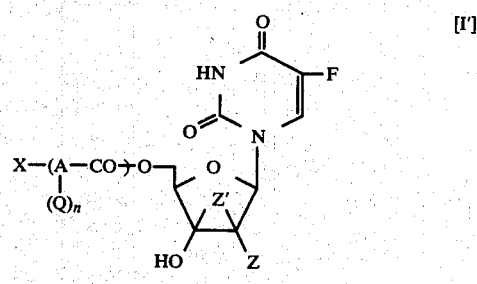

wherein A, Q, X, Z, Z' and n have the same meanings as given above, with a nitrogen-containing compound of the general formula:

wherein B has the same meaning as given above and Y stands for a radical capable of being reacted with X and split off as X-Y upon condensation, splitting off any protecting group from the resultant product, and if desired, converting the free compound into a physiologically acceptable salt or vice versa.

In this embodiment, the end product is obtained in two steps, by esterification followed by condensation. In the first esterification step, the reaction between the nucleoside of the general formula (II) and the fatty acid of the general formula (III') is carried out in the same manner as described in the firstly mentioned embodiment. More precisely, the nucleoside is an esterification reaction with the fatty acid of the general formula (III') optionally in the form of a reactive functional derivative thereof in an anhydrous aprotic solvent in the presence of a basic substance and a condensing agent which is excluded when the fatty acid is used in the form of a reactive functional derivative thereof, under the same conditions as described in the firstly mentioned embodiment.

In the fatty acid of the general formula (III'), the radical X replaceable with the nitrogen-containing group B is a halogen atom such as Br, I or Cl or a sulfonyloxy group such as p-toluenesulfonyloxy group or methanesulfonyloxy group. The radical X can be introduced into the fatty acid by direct halogenation of the fatty acid with a halogenating agent or by treating the fatty acid containing the hydroxy group in the desired position in a usual manner with a hydrogen halide such as hydrogen chloride or hydrogen bromide, or a sulfonyl chloride such as p-toluenesulfonyl chloride or methanesulfonyl chloride.

The preparation of the saturated fatty acid carrying the hydroxyl group in the desired position is generally known. Concerning the fatty acid of the general formula (III') the preparation of which is not described in the literature, it can be prepared in accordance with the method known for preparing analogous compounds.

In the second condensation step, the ester of the general formula (I') formed as an intermediate product is reacted with a compound of the general formula (IV) in a solvent under heating, if necessary, in the presence of a condensing agent. In the compound of the general formula (IV), the radical Y is a hydrogen atom or an alkali metal in the form of a salt.

Examples of the solvent utilizable for this condensation reaction include water, a lower alcohol such as methanol or ethanol, a ketone such as acetone, an ether such as dioxane, dimethylformamide and the like polar solvents which are soluble in or miscible with water. A mixture of these solvents may also be used.

The reaction is effected at a temperature of 40°-100° C. and is completed within the period of 3-25 hours under such condition.

In the above two alternative embodiments of the process, a part or all of the hydroxy groups in positions other than the 5'-position of the starting nucleoside are preferably blocked with a protective group of the previously mentioned type to prevent any side reaction. This protecting treatment prior to the reaction is indeed recommendable to attain the preparation of the end product in a high yield without the necessity of any troublesome after-treatment for separation from analogous products. In such case, the resultant ester is subjected to hydrolysis or hydrogenolysis to split off the protective group prior to the purification treatment of the end product. The hydrolysis or catalytic hydrogenolysis for this purpose is carried out in a manner known per se. In case of hydrolysis, the resultant ester is treated with an acid in a proper solvent at a temperature preferably below 40° C. Illustrative of the acid are, for example, a mineral acid such as hydrochloric acid or sulfuric acid and an organic acid such as acetic acid or trifluoroacetic acid. The use of trifluoroacetic acid is preferable. Examples of the solvent in this after-treatment include protic solvents such as water, a lower alcohol such as methanol or ethanol, formic acid, acetic acid and a mixture of these. In some cases, an aprotic solvent may be used preferably in combination with the protic solvent. The reaction time for completion of the hydrolysis is usually within the period from 30 minutes to 20 hours.

In case the protective group is split off by catalytic hydrogenolysis, the reaction is carried out in a usual manner, for example, in a proper solvent by the aid of a hydrogenation catalyst such as palladium-carbon or, Raney metal. This method is particularly preferably applied if the protective group is benzyloxycarbonyl or the like aralkyloxycarbonyl group. Examples of the solvent in this case include protic solvents such as methanol, ethanol and isopropanol and aprotic solvents such as benzene, toluene, xylene, dichloromethane, chloroform, dichloroethane, dialkyl ethers and dioxane. The reaction is usually carried out at room temperature or at a somewhat elevated temperature when a Raney metal such as Raney nickel is used. The use of palladium-carbon is preferable.

The nitrogen-containing group in the resultant ester may be converted, if desired, into other kinds of nitrogen-containing groups. For example, the new nucleoside derivatives of this invention carrying the free amino group as the nitrogen-containing group can be converted by N-acylation into the new nucleoside derivatives carrying an N-acylamino group as the nitrogen-containing group. The N-acylation in this case is carried out according to a usual method, for example, by dissolving the new nucleoside derivative carrying the free amino group in a solvent and treating the derivative with an acid halide or anhydride in the presence of a basic substance. Examples of the solvent preferably used for the N-acylation include benzene, toluene, xylene, dichloromethane, chloroform, dichloroethane, ethers, dioxane and the like aprotic solvents. Preferable examples of the basic substance include tertiary amines such as trialkylamine, pyridine and alkyl-substituted pyridine, e.g. picoline, lutidine and collidine; and inorganic bases such as sodium hydrogen carbonate, potassium carbonate and barium carbonate.

Similarly, the new nucleoside derivatives carrying the free amino group may be N-alkylated according to a method known per se or converted into other amino derivatives, if so desired.

The crude end product obtained by either of the two embodiments can be separated from contaminants and purified by way of chromatography or recrystallization from a proper organic solvent such as chloroform. The purification by way of chromatography (column chromatography or TLC) is conducted in a usual manner, for example, by using silica gel as adsorbent and chloroform, methanol, carbon tetrachloride or a mixture of these solvents as developer.

The new nucleoside derivatives of the present invention can be obtained as is or converted into physiologically acceptable acid-addition salts thereof with an acid. Examples of the acid utilizable for this purpose include mineral acids such as hydrochloric acid, hydrobromic acid, sulfuric acid and nitric acid; and organic acids such as p-toluenesulfonic acid and methanesulfonic acid. In general, such an acid-addition salt can be prepared by dissolving the free compound obtained by either of the two embodiments in a proper solvent, adding an equimolar amount of an acid and then evaporating the solvent. In case of the nucleoside derivative carrying the free amino group as the nitrogen-containing group, an acid is preferably allowed to be present in the reaction system, for example, in the catalytic hydrogenation treatment by the aid of palladiumcarbon whereby the product can be obtained directly in the form of an acid-addition salt. In case of the process wherein the product can be obtained directly as a salt, the ester linkage of the resultant product can conveniently be protected from hydrolysis.

In case the fatty acid of the general formula (III) is in the form of a salt, the nucleoside derivatives can be obtained also in the form of a salt. Then, the salt may be converted, if desired, into the free compound or into a different salt. If optical isomers exist in the fatty acid of the general formula (III) or (III'), the end product is obtained as an optically active isomer or racemic form. In case the product is obtained in a racemic form, it may be resolved, if desired, into an optically active isomer according to a usual optically resolving treatment by the aid of silica gel chromatography or an optically active reagent, such as d-camphorsulfonic acid.

The new nucleoside derivatives of the present invention exhibit a high level of anti-tumor activity with a very low toxicity. As a result of animal tests, it has been found that the new nucleoside derivatives of the present invention are superior to the starting nucleosides in anti-tumor activity to lymphatic leukemia L-1210 not only by intraperitoneal injection but also by oral administration.

In addition to the anti-tumor activity, the new nucleoside derivatives of the present invention were found to possess antivirus activity and immunosuppressing activity.

Thus, the new nucleoside derivatives of the present invention are useful as anti-tumor agents or intermediate products for preparing other useful derivatives.

The present invention will now be illustrated in more detail by way of examples and comparative examples. In these examples, the molar proportion of the reactants is shown in terms of millimol (m-mol). In Examples 11, 12, 13, 24, 25 and 27, the samples subjected to elementary analysis contained $0.5H_2O$, $0.5H_2O$, $1.0H_2O$, $1.5H_2O$, $1.0H_2O$ and $1.1H_2O$, respectively.

EXAMPLE 1

Preparation of 5'-O-(N-propylcarbamoylalanyl)-5-fluorouridine

In pyridine (15 ml) were dissolved 2.5 g (8.28 m-mol) of 2',3'-O-isopropylidine-5-fluorouridine and 2.88 g (16.56 m-mol) of N-propylcarbamoylalanine. To this solution was added under ice-cooling 5.0 g (16.56 m-mol) of 2,4,6-triisopropylbenzenesulfonyl chloride (referred to hereinafter simply as TPS), and the mixture was stirred for 18 hours at room temperature. The reaction liquid is concentrated under reduced pressure and the residue was taken up in chloroform (300 ml) and washed with a 2% aqueous solution (200 ml) of sodium hydrogen carbonate and then with water (200 ml). The organic phase was dried over $Na_2SO_4$ and concentrated and the residue was subjected to a separation treatment by way of a silica gel column chromatography [silica gel: Kiesergel H type (Merck); column size: 5×25 cm; developing solvent: chloroform-a linear gradient of chloroform containing 0→4% methanol under low pressure of 2-3 kg/cm²] whereby 2.83 g (yield: 74.6%)

of 5'-O-(N-propylcarbamoylalanyl)2',3'-O-isopropylidene-5-fluorouridine was obtained.

NMR (in CDCl₃) δ ppm: 0.88 (3H, t, CH₃CH₂), 1.33 (s) and 1.55 (s)

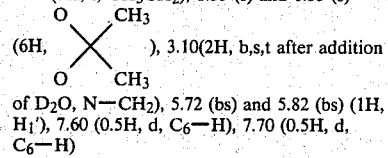

(6H, ), 3.10(2H, b,s,t after addition of D₂O, N—CH₂), 5.72 (bs) and 5.82 (bs) (1H, H₁'), 7.60 (0.5H, d, C₆—H), 7.70 (0.5H, d, C₆—H)

In a 90% aqueous solution (15 ml) of trifluoroacetic acid was dissolved 2.50 g (5.45 m-mol) of the ester obtained in the above treatment, and the solution was stirred for 30 minutes at room temperature. The reaction liquid was concentrated under reduced pressure and the residue was subjected to a separation-purification treatment by way of silica gel column chromatography (column size: 5×7 cm; developing solvent: chloroform containing 1-4% methanol) whereby 1.96 g of 5'-O-(N-propylcarbamoylalanyl)-5-fluorouridine was obtained as amorphous powders.

NMR (in CD₃OD) δppm: 0.90 (3H, t, CH₃CH₂—), 1.40 (3H, d, CH₃CH), 3.10 (2H, t, N—CH₂), 5.87 (1H, bs, H₁'), 7.85 (0.5H, d, C₆-H), 7.90 (0.5H, d, C₆-H)

EXAMPLE 2

Preparation of 5'-O-(N-butylcarbamoylalanyl)-5-fluorouridine

In pyridine (15 ml) were dissolved 2.5 g (8.28 m-mol) of 2',3'-O-isopropylidine-5-fluorouridine and 3.1 g (16.56 m-mol) of N-butylcarbamoylalanine. To this solution was added under ice-cooling 5.0 g (16.56 m-mol) of TPS, and the mixture was stirred for 18 hours at room temperature. The reaction liquid is concentrated under reduced pressure and the residue was taken up in chloroform (300 ml) and washed with a 2% aqueous solution (200 ml) of sodium hydrogen carbonate and then with water (200 ml). The organic phase was dried over Na₂SO₄ and concentrated and the residue was subjected to a separation-purification treatment by way of silica gel column chromatography [silica gel: Kiesergel H type (Merck); column size: 5×25 cm; developing solvent: chloroform - a linear gradient of chloroform containing 4% methanol under low pressure of 2–3 kg/cm²] whereby 3.48 g (yield: 89%) of 5'-O-(N-butylcarbamoylalanyl)-2',3'-O-isopropylidene-5-fluorouridine was obtained.

NMR (in CDCl₃) δ ppm: 0.90 (3H, t, CH₃CH₂), 1.37 (s) and 1.58 (s)

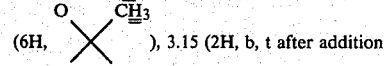

(6H, ), 3.15 (2H, b, t after addition of D₂O, N—CH₂), 5.72 (bs) and 5.82 (bs) (1H, H₁'), 7.60 (0.5H, d, C₆—H), 7.70 (0.5H, d, C₆—H)

In a 90% aqueous solution (20 ml) of trifluoroacetic acid was dissolved 3.40 g (7.20 m-mol) of the ester obtained in the above treatment, and the solution was stirred for 30 minutes at room temperature. The reaction liquid was concentrated and the residue was subjected to a separation-purification treatment by way of silica gel column chromatography (column size: 5×10 cm; developing solvent: chloroform containing 1-4% methanol) whereby 2.53 g of 5'-O-(N-butylcarbamoylalanyl)-5-fluorouridine was obtained as amorphous powders.

NMR (in CD₃OD) δ ppm: 0.92 (3H, t, CH₃CH₂), 1.40 (3H, d, CH₃CH), 3.13 (2H, t, N-CH₂), 5.88 (1H, bs, H₁'), 7.86 (0.5H, d, C₆-H), 7.90 (0.5H, d, C₆-H).

EXAMPLE 3

Preparation of 5'-O-(N-benzyloxycarbonylmethionyl)-5-fluorouridine

940 Milligrams (3.3 m-mol) of N-benzyloxycarbonylmethionine and 530 mg (1.7 m-mol) of 2',3'-O-ethoxyethylidene-5-fluorouridine were azeotropically dehydrated three times with 5 ml of anhydrous pyridine and then dissolved in anhydrous pyridine. To this solution was added 1.0 g (3.3 m-mol) of TPS, and the mixture was stirred for 20 hours at room temperature to effect condensation reaction. The solvent was removed by distillation under reduced pressure and the residue was distributed in a mixture of 100 ml of chloroform and 100 ml of water (This aqueous phase was kept at a pH value of 7.5–8 with solid sodium carbonate.). The chloroform layer was dried with anhydrous sodium sulfate and filtered. The chloroform was removed by distillation under reduced pressure and the residue was dissolved in 3 ml of chloroform, adsorbed to 20 g of silica gel and then developed with chloroform containing 1% methanol whereby 970 mg of 5'-O-(N-benzyloxycarbonylmethionyl)-2', 3'-O-ethoxyethylidene-5-fluorouridine was obtained.

NMR (in DMSO—d₆)* δ ppm: 11.46 (bs, 1H, H₃), 8.08 (d, 1H, H₆), 7.30 (s, 5H, 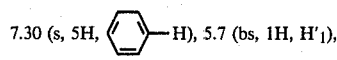—H), 5.7 (bs, 1H, H'₁), 5.10 (s, 2H, ⌬—CH₂—), 3.6 (bq, 2H, CH₂—CH₂—O—), 2.6 (s, 3H, CH₃—S—), 1.2 (m, 3H, CH₃—CH₂—O—).

*DMSO stands for dimethylsulfoxide.

This ester was then dissolved in 15 ml of ethanol. To this solution were added 3 ml of a 90% aqueous solution of formic acid and 7 ml of water, and the mixture was subjected to reaction at room temperature for 20 hours. The solvents were removed by distillation under reduced pressure from the reaction mixture and the residue was dissolved in 3 ml of chloroform, adsorbed to 15 g of silica gel and developed with chloroform containing 3% methanol whereby 790 mg of 5'-O-N-benzyloxycarbonylmethionyl-5-fluorouridine was obtained as a colorless caramel.

NMR (in CD₃OD) δ ppm:

7.75 (d, H₆), 7.28 ( 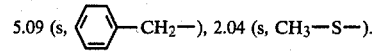—H), 5.81 (bs, H'₁), 5.09 (s, ⌬—CH₂—), 2.04 (s, CH₃—S—).

Mass Spectroanalysis: 528 (M⁺), 397, 398, 130
Elementary analysis: as C₂₂H₂₇N₃O₉FS

| | C | H | N |
|---|---|---|---|
| Found: | 49.85% | 5.02% | 7.94% |

NMR (in CD₃OD) δ ppm: 7.75 (d, H₆), 7.28 (⌬—H), 5.81 (bs, H'₁),
5.09 (s, ⌬—CH₂—), 2.04 (s, CH₃—S—).

Mass Spectroanalysis: 528 (M⁺), 397, 398, 130
Elementary analysis: as $C_{22}H_{27}N_3O_9FS$

|  | C | H | N |
|---|---|---|---|
| Calc.: | 50.00% | 5.15% | 7.95% |

EXAMPLE 4
Preparation of 5'-O-(N-decanoylmethionyl)-5-fluorouridine

In 7 ml of anhydrous pyridine were dissolved 1.00 g (3.30 m-mol) and 2.00 g (6.60 m-mol) of N-decanoylmethionine. To this solution was added 2.00 g (6.60 m-mol) of TPS, and the mixture was subjected to condensation reaction at room temperature for 44 hours. The solvent was removed by distillation under reduced pressure and the residue was distributed in a mixture of 100 ml of chloroform and 100 ml of water (This aqueous phase was kept at a pH value of 7.5–8 with solid sodium carbonate.). The chloroform layer was dried with anhydrous sodium sulfate and filtered and the chloroform was removed by distillation under reduced pressure.

The residue was dissolved in 5 ml of chloroform, adsorbed to 150 g of silica gel and developed with chloroform containing 1% methanol whereby 1.17 g of 5'-O-(N-decanoylmethionyl)-2',3'-O-isopropylidene-5-fluorouridine was obtained as a colorless caramel.

NMR (in CDCl₃) δ ppm: 10.3 (bs, 1H, 3H), 7.70 (d, 0.5H, H₆),
7.60 (d, 0.5H, H₆), 5.85 (bs, 0.5H, H₁'),
5.70 (bs, 0.5H, H₁'), 2.10 (s, 3H, C$\underline{H}_3$—S—),
1.61, 1.42 (s, s, 3H × 2, (CH₃)₂C ), 1.25 (bs,
14H, —(C$\underline{H}_2$)₇—), 0.90 (bt, 3H, —CH₂—C$\underline{H}_3$)

In 5 ml of a 90% aqueous solution of trifluoroacetic acid was dissolved 970 mg (1.65 m-mol) of this ester, and the solution was stirred for 1 hour at room temperature to effect reaction.

The reaction liquid was concentrated under reduced pressure and the residue was taken up in 5 ml of chloroform, adsorbed to 20 g of silica gel and then developed with chloroform containing 3% methanol whereby 750 mg of 5'-O-(N-decanoylmethionyl)-5-fluorouridine was obtained.

M.P. 133°–136° C. (after crystallization from isopropanol).

NMR (in CD₃OD) δppm: 8.00 (d) and 7.79 (d) (H₆), 5.93 (bs, H₁'), 2.10 (C$\underline{H}_3$—S—), 1.30 (bs, —C$\underline{H}_2$—), 0.90 (bt, —CH₂—C$\underline{H}_3$).

Mass spectroanalysis: 547 (M⁺), 418, 130.
Elementary analysis: as $C_{24}H_{38}N_3O_8SF$

|  | C | H | N |
|---|---|---|---|
| Found: | 52.74% | 6.85% | 7.81% |
| Calc.: | 52.64% | 6.99% | 7.67% |

EXAMPLE 5
Preparation of 5'-O-[N-(3-phenylpropionyl)methionyl]-5-fluorouridine In 20 ml of anhydrous pyridine were dissolved 940 mg (3.35 m-mol) of N-(3-phenylpropionyl)methionine and 600 mg (1.99 m-mol) of 2',3'-O-isopropylidene-5-fluorouridine. To this solution was added 1.00 g (3.31 m-mol) of TPS and the mixture was subjected to a condensation reaction at room temperature for 4.5 hours. The reaction mixture was worked up in the same manner as described in Example 3 or 4 whereby 350 mg of 5'-O-[N-(3-phenylpropionyl)methionyl]-2',3'-O-isopropylidene-5-fluorouridine was obtained as a colorless caramel.

NMR (in CDCl₃) δ ppm: 7.54 (d, 0.5H, H₆), 7.44 (d, 0.5H, H₆),
7.21 (s, 5H, ⌬—H), 5.71 (d, 0.5H, H'₁),
5.58 (d, 0.5H, H'₁), 2.03 (s, 3H, CH₃—S—),
1.55 (s) and 1.34 (s) (s, s, 3H × 2, (CH₃)₂C )

In 2 ml of a 90% aqueous solution of trifluoroacetic acid was dissolved 440 mg (1.20 m-mol) of the ester obtained in the above reaction. The mixture was subjected to reaction at room temperature for 1 hour and the reaction mixture was worked up in accordance with the method as described in Example 3 or 4 whereby 300 mg of 5'-O-[N-(3-phenylpropionyl)methionyl]-5-fluorouridine was obtained as a colorless caramel.

NMR (in CD₃OD) δ ppm: 7.82 (d) and 7.79 (d) (H₆), 7.20 (⌬—H),
5.84 (bs, H'₁), 2.00 (CH₃—S—).

Mass spectroanalysis: 525 (M⁺), 394, 130
Elementary analysis: as $C_{23}H_{28}N_3O_8FS$ (M.W. 525.55)

|  | C | H | N |
|---|---|---|---|
| Found: | 52.64% | 5.56% | 8.11% |
| Calc.: | 52.56% | 5.37% | 8.00% |

EXAMPLE 6
Preparation of 5'-O-(N-pentanoylmethionyl)-5-fluorouridine 3.00 Grams (12.9 m-mol) of N-pentanoylmethionine and 1.94 g (6.44 m-mol) of 2',3'-O-isopropylidene-5-fluorouridine was azeotropically dehydrated with anhydrous pyridine and then dissolved in 40 ml of anhydrous pyridine. To this solution was added 5.50 g (18.2 m-mol) of TPS and the mixture was subjected at room temperature to condensation reaction for 25 hours. The reaction mixture was worked up in accordance with the method as described in Example 3 or 4 whereby 1.39 g of 5'-O-(N-pentanoylmethionyl)-2',3'-O-isopropylidene-5-fluorouridine was obtained as a colorless caramel.

| NMR (in CDCl₃) δ ppm: | 7.62 (d, 0.5H, H₆), 7.42 (d, 0.5H, H₆), 5.77 (bd, 0.5H, H'₁), 5.62 (bd, 0.5H, H'₁), 2.07 (s, 3H, —S—CH₃), 1.56 (s) and 1.36 (s) (3H × 2, $\overset{CH_3}{\underset{CH_3}{>C<}}$), 0.90 (bt, 3H, —CH₂—CH₃) |
|---|---|

In 4 ml of chloroform was dissolved 1.01 g (1.95 m-mol) of the ester obtained in the above reaction. To this solution was added 20 ml of a 90% aqueous solution of trifluoroacetic acid, and the mixture was subjected to reaction at room temperature for 1.5 hours. The reaction mixture was then worked up in the same manner as described in Example 3 or 4 whereby 840 mg of 5'-O-(N-pentanoylmethionyl)-5-fluorouridine was obtained as a colorless caramel.

| NMR (in CD₃OD) δ ppm: | 7.86 (d) and 7.82 (d) (H₆), 5.83 (bs, H'₁), 2.08 (—S—CH₃), 1.5 (m, —CH₂—), 0.91 (CH₂—CH₃). |
|---|---|
| Mass spectroanalysis: | 477 (M⁺), 347, 130 |
| Elementary analysis: | as C₁₉H₂₈N₃O₈SF (M.W. 477.51) |

| | C | H | N |
|---|---|---|---|
| Found: | 47.61% | 5.97% | 8.52% |
| Calc.: | 47.79% | 5.91% | 8.80% |

EXAMPLE 7
Preparation of 5'-O-(N-benzyloxycarbonylprolyl)-5-fluorouridine

In 14 ml of anhydrous pyridine were dissolved 3.30 g (13.2 m-mol) of N-benzyloxycarbonylproline and 2.00 g (6.6 m-mol) of 2',3'-O-isopropylidene-5-fluorouridine. To this solution was added 4.00 g (13.2 m-mol) of TPS, and the mixture was stirred for 3 hours at room temperature to effect condensation reaction. This reaction mixture was worked up in the same manner as described in Example 3 or 4 whereby 3.00 g of 5'-O-(N-benzyloxycarbonylprolyl)-2',3'-O-isopropylidene-5-fluorouridine was obtained.

| NMR (in CDCl₃) δ ppm: | 10.0 (bs, 1H, H₃), 7.35 (bs, 6H, —⌬—H and H₆), 5.85 (bs, 0.5H, H'₁), 5.75 (bs, 0.5H, H'₁), 5.20 (s, 2H, ⌬—CH₂—), 3.60 (bt, 2H, —N<CH₂—), 2.1 (m, 4H, —CH₂—), 1.60 (s, 3H, $\overset{CH_3}{>C<}_{CH_3}$), 1.40 (s, 3H, $\overset{CH_3}{>C<}_{CH_3}$). |
|---|---|

In 12 ml of a 90% aqueous solution of trifluoroacetic acid was dissolved 3.06 g (5.74 m-mol) of the ester obtained in the above reaction. The mixture was stirred for 1.5 hours at room temperature to effect reaction and the reaction mixture was then worked up in accordance with the method as described in Example 3 or 4 whereby 1.63 g of 5'-O-(N-benzyloxycarbonylprolyl)-5-fluorouridine was obtained.

M.P. 137°–144° C. (after crystallization from isopropanol).

| NMR (in CD₃OD) δ ppm: | 7.75 (d) and 7.90 (d) (H₆), 5.90 (bs, H'₁), 5.13 (s) and 5.18 (s) (⌬—CH₂—), 3.60 (bt, >N—CH₂—), 2.1 (m, —CH₂—). |
|---|---|
| Mass spectroanalysis: | 493 (M⁺), 358, 130 |
| Elementary analysis: | as C₂₂H₂₄N₃O₉F |

| | C | H | N |
|---|---|---|---|
| Found: | 53.44% | 4.89% | 8.59% |
| Calc.: | 53.55% | 4.90% | 8.52% |

EXAMPLE 8
Preparation of 5'-O-(benzyloxycarbonylvalyl)-5-fluorouridine 3.51 Grams (13.98 m-mol) of N-benzyloxycarbonylvaline and 2.72 g (9.00 m-mol) of 2',3'-O-isopropylidene-5-fluorouridine were azeotropically dehydrated with anhydrous pyridine and then dissolved in 50 ml of anhydrous pyridine. To this solution was added 5.40 g (17.82 m-mol) of TPS, and the mixture was subjected to reaction at room temperature for 20 hours. This reaction mixture was worked up in the same manner as described in Example 3 or 4 whereby 3.62 g of 5'-O-(N-benzyloxycarbonylvalyl)-2',3'-O-isopropylidene-5-fluorouridine was obtained as a colorless caramel.

| NMR (in CDCl₃, TMS) δ ppm: | 7.40 (s and d, 6H, —⌬—H and H₆), 5.63 (d, 1H, H'₁), 5.18 (s, 2H, ⌬—CH₂—), 5.0 (m, 2H, H'₂ and H'₃), 4.4 (bs, 4H, H'₅, H'₄ and >N—CH—), 2.2 (m, 1H, —CH—), 1.58 (s) and 1.46 (s) (3H × 2, $\overset{CH_3}{>C<}_{CH_3}$), 0.92 (d, d, 6H, $\overset{CH_3}{>C<}_{CH_3}$) |
|---|---|

In 4 ml of chloroform was dissolved 3.49 g of the ester obtained in the above reaction. To this solution was added 10 ml of a 90% aqueous solution of trifluoroacetic acid, and the mixture was subjected to reaction at room temperature for 3 hours. The reaction mixture was worked up in accordance with the method as described in Example 3 or 4 whereby 2.11 g of 5'-O-(N- benzyloxycarbonylvalyl)-5-fluorouridine was obtained as a colorless caramel.

NMR (in CD₃OD) δ ppm: 7.87 (d, H₆), 7.39 (s, 5H, —C₆H₅—H), 5.87 (bd, H'₁), 5.13 (s, C₆H₅—CH₂—), 2.20 (m, —CH(CH₃)₂), 0.98 (d, —CH—CH₃).

Mass spectroanalysis: 495 (M⁺), 365, 130

Elementary analysis: as $C_{22}H_{26}N_3O_9F \cdot H_2O$

| | C | H | N |
|---|---|---|---|
| Found: | 51.56% | 5.25% | 7.82% |
| Calc.: | 51.46% | 5.50% | 8.18% |

EXAMPLE 9

Preparation of 5'-O-(N-butyrylvalyl)-5-fluorouridine

To an isopropanolic solution (93.5 ml) of 2.20 g (4.11 m-mol) of 5'-O-(N-benzyloxycarbonylvalyl)-2',3'-O-isopropylidene-5-fluorouridine obtained in Example 8 were added a solution (3.80 g) of 3.7% (wt/wt) hydrogen chloride-isopropanol and 10% palladium-carbon (1.60 g), and the mixture was stirred in a stream of hydrogen under normal pressure for 3 hours at ordinary temperatures. After the reaction, the catalyst was filtered off and the solvent was removed by distillation under reduced pressure from the filtrate. 5'-O-valyl-2',3'-O-isopropylidene-5-fluorouridine hydrochloride obtained as the residue was dissolved in dichloromethane (30 ml), and 0.83 g (7.76 m-mol) of 2,6-lutidine was added to this solution. To this solution under ice-cooling was added dropwise a solution of 0.41 g (3.85 m-mol) of butyl chloride in dichloromethane (10 ml). To this reaction mixture were added ice water (25 ml) and chloroform (40 ml), and the organic phase was separated from the aqueous phase and washed with a 2% aqueous solution of sodium hydrogen carbonate (50 ml×2) and then with water (50 ml×2). After drying the organic phase over Na₂SO₄, the solvents were distilled off under reduced pressure and the residue was subjected to a separation-purification treatment by way of silica gel column chromatography (column size: 2.54×7.0 cm; developers: chloroform-carbon tetrachloride 1:1, chloroform-methanol 99:1) whereby 1.00 g (yield: 54.6%) of 5'-O-(N-butyrylvalyl)-2',3'-O-isopropylidene-5-fluorouridine was obtained as amorphous powders.

NMR (in CDCl₃) δ ppm: 7.43 (1H, d, H₆), 6.19 (1H, d, CH—NH—C(=O)—), 5.57 (1H, d, H'₁), 1.55 (3H, s, C(CH₃)₂), 1.35 (3H, s, C(CH₃)₂).

To 1.00 g (2.12 m-mol) of the ester obtained in the above treatment was added a 90% aqueous solution (20 ml) of trifluoroacetic acid, and the mixture was stirred for 30 minutes at room temperature. The solvent was removed by distillation under reduced pressure and the residue was subjected to a separation-purification treatment by way of silica gel column chromatography (column size: 1.0×20 cm; developing solvent: chloroform-methanol 97:3) whereby 0.71 g of 5'-O-(N-butyrylvalyl)-5-fluorouridine was obtained as amorphous powders.

NMR (CD₃OD) δ ppm: 7.82 (1H, d, H₆), 5.78 (1H, d, H'₁), 0.96 (6H, d, —CH(CH₃)₂)

Elementary analysis: as $C_{18}H_{26}N_3O_8F$ (M.W. 431.42)

| | C | H | N |
|---|---|---|---|
| Found: | 49.94% | 6.20% | 9.36% |
| Calc.: | 50.11% | 6.07% | 9.74% |

EXAMPLE 10

Preparation of 5'-O-(N-propionylvalyl)-5-fluorouridine

In dichloromethane (130 ml) was dissolved 3.57 g (8.16 m-mol) of 5'-O-valyl-2',3'-O-isopropylidene-5-fluorouridine hydrochloride obtained in Example 9. To this solution was added 1.92 g (17.95 m-mol) of 2,6-lutidine, and a solution of 0.83 g (8.97 m-mol) of propionyl chloride in dichloromethane (20 ml) was added dropwise to the mixture under ice-cooling. The reaction liquid was washed with water (100 ml) and the organic phase was dried over Na₂SO₄ and then concentrated under reduced pressure. The residue was subjected to a separation-purification treatment by way of silica gel column chromatography (column size: 3×10 cm; developing solvent: chloroform containing 1→4% methanol) whereby 2.49 g (yield: 66.6%) of 5'-O-(N-propionylvalyl)-2',3'-O-isopropylidene-5-fluorouridine was obtained.

NMR (CDCl₃) δ ppm: 0.90 (d) and 0.95 (d) (6H, CH(CH₃)₂), 1.18 (3H, t, CH₃CH₂—), 1.58 (s) and 1.37 (s) (6H, C(CH₃)₂O,O), 2.30 (3H, m, CH(CH₃)₂), CH₃CH₂—), 5.88 (1H, d, H'₁), 6.12 (1H, d, NH), 7.42 (1H, d, C₆—H), 9.30 (1H, b, N₃—H).

In a 90% aqueous solution (10 ml) of trifluoroacetic acid was dissolved 2.00 g (4.38 m-mol) of the ester obtained in the above treatment, and the solution was stirred for 30 minutes at room temperature. The reaction liquid was concentrated under reduced pressure and the residue was subjected to a separation-purification treatment by way of silica gel column chromatography (column size: 3×12 cm; developing solvent: chloroform containing 1→4% methanol) whereby 1.55 g of 5'-O-(N-propionylvalyl)-5-fluorouridine was obtained as amorphous powder.

NMR (CD₃OD) δ ppm: 0.97 (6H, d, —CH(CH₃)(CH₃)), 1.12 (3H, t, CH₃—CH₂), 2.23 (3H, m, —CH(CH₃)(CH₃) CH₃—CH₂—), 5.80 (1H, bd, H'₁), 7.85 (1H, d, C₆—H)

Elementary analysis: as $C_{17}H_{24}N_3O_8F$ (M.W. 417,39)

|  | C | H | N |
|---|---|---|---|
| Found: | 47.38% | 5.51% | 10.42% |
| Calc.: | 48.92% | 5.79% | 10.07% |

EXAMPLE 11

Preparation of 5'-O-(N-tiglylvalyl)-5-fluorouridine

In methylene chloride (80 ml) were dissolved 2.20 g (5.03 m-mol) of 5'-O-valyl-2',3'-O-isopropylidene-5-fluorouridine hydrochloride obtained in Example 9 and 1.35 g (12.6 m-mol) of 2,6-lutidine. A solution of 0.89 g (7.5 m-mol) of tiglyl chloride in methylene chloride (3 ml) was added dropwise to the above mixture under ice-cooling. After addition of the tiglyl chloride, the mixture was stirred for 4 hours at room temperature. The reaction liquid was washed with a 2% aqueous solution (70 ml) of potassium carbonate and the methylene chloride layer was dried with Na₂SO₄, filtered and concentrated under reduced pressure. The residue was subjected to a separation-purification treatment by way of silica gel column chromatography (column size: 3×20 cm; developing solvents: chloroform-carbon tetrachloride (1:1), chloroform and chloroform containing 0.5% methanol) whereby 1.89 g of 5'-O-(N-tiglylvalyl)-2',3'-O-isopropylidene-5-fluorouridine was obtained.

NMR (in CDCl₃) δ ppm: 7.55 (bd, 1H, H₆), 6.4 (m, 2H, CH₂=C(CH₃)(NH)), 5.70 (bs, 1H, H'₁), 1.84 (s, CH₃—CH=C(CH₃)), 1.78 (d, CH₂—CH=C(CH₃)), 1.55 (s) and 1.36 (s) (6H, C(CH₃)(CH₃)), 0.96 (d, 6H, C(CH₃)(CH₃)).

In 10 ml of a 90% aqueous solution of trifluoroacetic acid was dissolved 1.65 g (3.42 m-mol) of the ester obtained in the above treatment, and the solution was stirred for 1.5 hours at room temperature. The reaction liquid was concentrated under reduced pressure and the residue was subjected to a separation-purification treatment by way of silica gel column chromatography (column size: 3×12 cm; developing solvents: chloroform and chloroform containing 3% methanol) whereby 1.08 g of 5'-O-(N-tiglylvalyl)-5-fluorouridine was obtained as a colorless caramel.

NMR (in CD₃OD) δ ppm: 7.8 (d, 1H, H₆), 6.4 (bq, 1H, CH(CH₃)(CH₃)—C), 5.8 (bs, 1H, H'₁), 1.85 (s, C(CH₃)=C(CH₃)(H)), 1.8 (d, CH₂(H)=C(CH₃)), 1.0 (d, 6H, C(CH₃)(CH₃)), Elementary analysis: as $C_{19}H_{26}N_3O_8F$ (M.W. 443, 43)

|  | C | H | N |
|---|---|---|---|
| Found: | 50.13% | 5.93% | 9.32% |
| Calc.: | 50.44% | 6.01% | 9.29% |

EXAMPLE 12

Preparation of 5'-O-(N-hexanoylvalyl)-5-fluorouridine

To a solution of 4.00 g (7.48 m-mol) of 5'-O-(N-benzyloxycarbonylvalyl)-2',3'-O-isopropylidene-5-fluorouridine in isopropanol (110 ml) were added 10% palladium-carbon (2.50 g) and a solution (6.90 g) of 3.7 wt/wt % hydrogen chloride-isopropanol and the mixture was stirred in a stream of hydrogen under normal pressure at ordinary temperature for 3 hours.

The catalyst was filtered off from the hydrogenated product and the solvent was distilled off under reduced pressure. The residue was taken up in dichloromethane (60 ml) and 1.70 g (15.9 m-mol) of 2,6-lutidine was added thereto. This solution was ice-cooled and a solution of 1.04 g (7.97 m-mol) of hexanoyl chloride in dichloromethane (10 ml) was added dropwise thereto over the period of 30 minutes. Ice water (100 ml) was added to the reaction liquid, which was then extracted with chloroform (40 ml×3). The organic phase was washed with a 0.5% aqueous solution of potassium carbonate (50 ml×4) and then with water (50 ml×4), dried with Na₂SO₄ and concentrated under reduced pressure to remove the solvent. The residue was subjected to a separation-purification treatment by way of silica gel column chromatography [column size: 2.54×10.0 cm; developing solvent: chloroform-carbon tetrachloride (2:1)] whereby 2.24 g (yield: 60%) of 5'-O-(N-hexanoylvalyl)-2',3'-O-isopropylidene-5-fluorouridine was obtained.

NMR (in CDCl₃) δ ppm: 7.45 (1H, d, H₆), 6.32 (1H, d, —CO—NH—), 5.60 (1H, bs, H'₁),

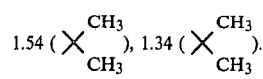

To 2.21 g (4.42 m-mol) of the product obtained in the above treatment was added a 90% aqueous solution (23 ml) of trifluoroacetic acid, and the solution was stirred for 30 minutes at room temperature. The solvent was removed by distillation under reduced pressure from the solution and the residue was subjected to a separation-purification treatment by way of silica gel column chromatography [column size: 2.0×30 cm; developing solvent: chloroform-methanol (97:3)] whereby 1.13 g of 5'-O-(N-hexanoylvalyl)-5-fluorouridine was obtained as amorphous powders.

NMR (in CD₃OD) δppm: 7.86 (1H, d, H₆), 5.84 (1H, bs, H₁').

Elementary analysis: as $C_{20}H_{30}N_3O_8F$ (M.W. 459, 47)

|  | C | H | N |
|---|---|---|---|
| Found: | 51.67% | 6.46% | 9.00% |
| Calc.: | 51.27% | 6.56% | 8.96% |

Mass Spectroanalysis: 459 (M+), 330, 130.

EXAMPLE 13

Preparation of 5'-valyl-5-fluorouridine hydrochloride

To a solution of 400 mg (0.81 m-mol) of 5'-O-(N-benzyloxycarbonylvalyl)-5-fluorouridine in isopropylalcohol (25 ml) were added 10% palladium-carbon (80 mg) and a solution (200 mg) of 16 wt/wt % hydrogen chloride-isopropyl alcohol, and the mixture was stirred in a stream of hydrogen under normal pressure at ordinary temperature for 22 hours.

The catalyst was filtered off from the hydrogenated product and the solvent was distilled off under reduced pressure. The residue was recrystallized from a small amount of isopropyl alcohol to obtain 180 mg of the end product.

M.P. 163°–166° C.

NMR (in CD₃OD) δ ppm: 7.48 (1H, d, H₆), 5.76 (1H, d, H'₁),

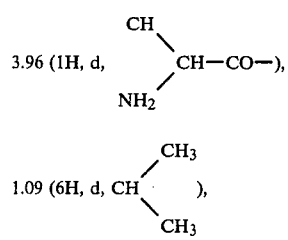

Elementary analysis: as $C_{14}H_{20}N_3O_7F \cdot HCl$ (N.W. 397, 79)

|  | C | H | N |
|---|---|---|---|
| Found: | 41.00% | 5.64% | 9.35% |
| Calc.: | 40.44% | 5.57% | 10.11% |

EXAMPLE 14

Preparation of 5'-O-(N-benzyloxycarbonylphenylalanyl)-5-fluorouridine

In 40 ml of anhydrous pyridine were dissolved 3.00 g (10.0 m-mol) of N-benzyloxycarbonylphenylalanine and 1.50 g (5.00 m-mol) of 2',3'-O-isopropylidene-5-fluorouridine. To this solution was then added 3.00 g (10.0 m-mol) of TPS, and the mixture was stirred for 2 hours at room temperature to effect a condensation reaction. The reaction mixture was then worked up in accordance with the method as described in Example 3 or 4 whereby 2.80 g of 5'-O-(N-benzyloxycarbonylphenylalanyl)-2',3'-O-isopropylidene-5-fluorouridine was obtained as a colorless caramel.

NMR (in CDCl₃) δ ppm: 7.39 (s) and 7.3 (m) (11H,

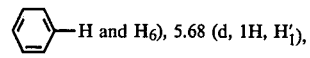—H and H₆), 5.68 (d, 1H, H'₁),

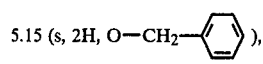

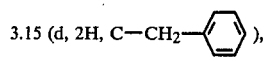

1.58 (s) and

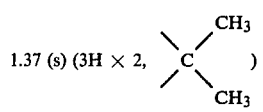

In 5 ml of a 90% aqueous solution of trifluoroacetic acid was dissolved 1.20 g of the resulting ester, and the solution was stirred for 30 minutes at room temperature to effect a hydrolytic reaction. The reaction mixture was then worked up in accordance with the method as described in Example 3 or 4 whereby 940 mg of 5'-O-(N-benzyloxycarbonylphenylalanyl)-5-fluorouridine was obtained as a colorless caramel.

NMR (in CD₃OD) δ ppm: 7.76 (d, H₆), 7.48 (s) and

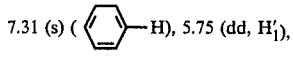

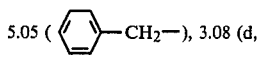

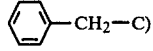

| Mass spectroanalysis: | 543 (M+), 414, 130 | | |
| Elementary analysis: | as $C_{26}H_{26}N_3O_9F$ (M.W. 543, 50) | | |
|  | C | H | N |
| Found: | 57.34% | 4.83% | 8.00% |
| Calc.: | 57.46% | 4.82% | 7.73% |

EXAMPLE 15

Preparation of 5'-O-(N-pentanoyltyrosyl)-5-fluorouridine

A solution of 6.0 g (50 m-mol) of pentanoyl chloride in ethyl ether (50 ml) and an aqueous solution (26 ml) of 2N-sodium hydroxide were added dropwise at the same time over the period of 30 minutes to an aqueous 2N-sodium hydroxide solution (38.5 ml) of 7.00 g (38.6 m-mol) of tyrosine under agitation at 5° C., while maintaining the pH value between 9 and 11. The mixture was stirred for an additional 2 hours at room temperature and, after addition of 2N-sodium hydroxide (5 ml) thereto, was warmed at 70° C. for 10 minutes. After cooling the reaction liquid at −10° C., 9.87 g (58m-mol) of benzyloxycarbonyl chloride and an aqueous 2N-sodium hydroxide solution (20.5 ml) were added dropwise at the same time to the reaction liquid under vigorous agitation. After completion of the reaction, 3N-hydrochloric acid was added to the reaction mixture to adjust the pH value to 3. A white precipitate formed was collected by filtration and recrystallized from chloroform whereby 12.80 g (yield: 82.9%) of N-pentanoyl-O-benzyloxycarbonyltyrosin was obtained.

NMR (DMSO—d6) δ ppm: 8.06 (1H, d, CH—NH—CO—), 7.42 (5H, s, 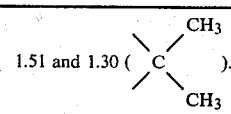—H), 7.30 (d) and 7.11 (d) (2H and 2H), 5.26 (2H, s,

⟨◯⟩—CH2—)

To a pyridine (50 ml) solution of 5.30 g (13.3 m-mol) of O-benzyloxycarbonyl-N-pentanoyltyrosin obtained in the above reaction were added dropwise at the same time 4.0 g (13.2 m-mol) of TPS and 2.10 g (6.95 g) of 2',3'-O-isopropylidene-5-fluorouridine, and the mixture was allowed to stand for 16 hours at room temperature. The solvent was distilled off under reduced pressure from the reaction mixture and the residue was taken up in benzene (140 ml) and the benzene solution was washed with a 3% aqueous solution of sodium hydrogen carbonate (100 ml×4) and then with water (100 ml×4). The organic phase was dried with Na2SO4 and concentrated under reduced pressure and the residue was then subjected to a separation-purification treatment by way of silica gel column chromatography [column size: 2.54×15.0 cm; developing solvents: chloroform-carbon tetrachloride (1:1) and chloroform] whereby 1.80 g (yield: 37.9%) of 5'-O-(O-benzyloxycarbonyl-N-pentanoyltyrosyl)-2',3'-isopropylidene-5-fluorouridine was obtained.

NMR (CDCl3) δ ppm: 7.39 (s, ⟨◯⟩—H), 6.36 (1H, m,

—CO—NH—), 5.62 (1H, d, H1'),

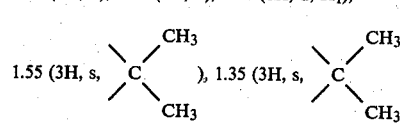

To a solution of 1.70 g (2.49 m-mol) of the resultant ester in isopropyl alcohol (20 ml) was added 10% palladium-carbon (400 mg), and the mixture was stirred for 2 hours in a stream of hydrogen under normal pressure at ordinary temperature. The catalyst was filtered off and the solvent was distilled off under reduced pressure from the reaction mixture, and the residue was subjected to a separation-purification treatment by way of silica gel column chromatography [column size: 2.54×10.0 cm; developing solvent: chloroform-methanol (98:2)] whereby 1.10 g (yield: 80.5%) of 5'-O-(N-pentanoyltyrosyl)-2',3'-O-isopropylidene-5-fluorouridine was obtained.

NMR (CDCl3 and CD3OD in a vol./vol. ratio of 5:1) δ ppm:
6.96 (2H, d), 6.70 (2H, d), 5.70 (1H, d, H1'),

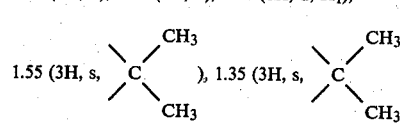

To 1.10 g (2.00 m-mol) of the ester obtained in the above treatment was added a 90% aqueous solution (12.0 ml) of trifluoroacetic acid, and the mixture was stirred for 30 minutes at room temperature. The solvent was removed by distillation under reduced pressure and the residue was subjected to a separation-purification treatment by way of silica gel column chromatography [column size: 2.0×30 cm; developing solvent: chloroform-methanol (96:4)] whereby 465 mg of 5'-O-(N-pentanoyltyrosyl)-5-fluorouridine was obtained as amorphous powders.

NMR (CD3OD) δ ppm: 7.85 (½ H, d, H6), 7.81 (½ H, d, H6), 7.02 (d) and 6.70 (d) (2H and 2H), 5.80 (1H, d, H1'), 2.98 (2H, d,

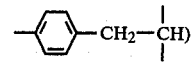—CH2—CH)

Elementary analysis: as C23H28N3O9F (M.W. 509, 49)

|  | C | H | N |
|---|---|---|---|
| Found: | 53.94% | 5.49% | 8.20% |
| Calc.: | 54.22% | 5.54% | 8.25% |

EXAMPLE 16

Preparation of 5'-O-(azidoacetyl)-5-fluorouridine (a) A solution of 0.7 g (4.47 m-mol) of bromoacetyl chloride in ethyl ether (3 ml) was added dropwise to a solution of 0.5 g (1.57 m-mol) of 2',3'-O-ethoxyethylidene-5-fluorouridine in anhydrous pyridine (20 ml) under vigouous agitation at 0° C. After addition of the chloride, the mixture was stirred for 1 hour at 0° C. The reaction liquid was poured into ice water and the resultant gummy product was taken up in 200 ml of chloroform and washed with 100 ml of a 5% aqueous solution of sodium hydrogen carbonate and then with water (100 ml×2). The chloroform layer was separated, dried with sodium sulfate and concentrated under reduced pressure after filtration.

The resultant residue was dissolved in 2 ml of dimethylformamide and 0.16 g (2.46 m-mol) of sodium azide and a catalytic amount of potassium iodide were added to the solution. The mixture was stirred for about 3.5 hours at room temperature and the reaction liquid was concentrated under reduced pressure and distributed in 200 ml of chloroform and 100 ml of water. The aqueous phase was extracted with chloroform and the washings were combined with the previously obtained chloroform phase. The combined chloroform phase was dried with sodium sulfate, filtered and concentrated whereby 0.34 g of 5'-O-(azidoacetyl)-2',3'-O-ethoxyethylidene-5-fluorouridine was obtained.

NMR (in CDCl$_3$) δ ppm: 7.56 (d, 1H, H$_6$), 5.86 (d, 0.5H, H$_1$'), 5.70 (d, 0.5H, H$_1$'), 4.0 (s, 2H, N$_3$—C$\underline{H}$$_2$—CO—O—) 3.71 (q, 1.5H, —C$\underline{H}$$_2$—CH$_3$), 3.60 (q, 1.5H, —C$\underline{H}$$_2$—CH$_3$), 1.22 (t, 1.5H, —CH$_2$—C$\underline{H}$$_3$), 1.20 (t, 1.5H, —CH$_2$—C$\underline{H}$$_3$).

IR (KBr) ν-N$^⊕$≡N 2100 cm$^{-1}$.

(b) In 20 ml of ethyl alcohol was dissolved 0.34 g of the azido ester obtained in the above step (a). To this solution was added 25 ml of a 30% aqueous solution of formic acid, and the mixture was allowed to stand for 21 hours at room temperature. The solvents were then distilled off under reduced pressure from the reaction mixture and the resultant residue was subjected to a separation-purification treatment by way of preparative thin layer chromatography (silica gel 30 g; developing solvent: ethyl acetate) whereby 0.12 g of 5'-O-azidoacetyl-5-fluorouridine was obtained as a colorless caramel.

NMR (in DMSO-d$_6$) δ ppm: 11.82 (bs, 1H, H$_3$), 7.89 (d, 1H, H$_6$), 5.70 (d, 1H, H$_1$'), 5.46 (d, 1H, 2' or 3'-O$\underline{H}$), 5.28 (d, 1H, 2' or 3'-O$\underline{H}$), 4.16 (s, 2H, N$_3$—C$\underline{H}$$_2$—CO—O—).

IR (KBr) ν-N$^⊕$≡N 2100 cm$^{-1}$.

Elementary analysis: as C$_{11}$H$_{12}$N$_5$O$_7$F (M.W. 345, 24)

|  | C | H | N |
|---|---|---|---|
| Found: | 38.04% | 3.73% | 20.53% |
| Calc.: | 38.27% | 3.50% | 20.29% |

EXAMPLE 17

Preparation of 5'-O-(2-azidopropionyl)-5-fluorouridine (a) At 0° C. 1.71 g (10 m-mol) of α-bromopropionyl chloride was added dropwise over the period of about 10 minutes to a solution of 2.00 g (6.62 m-mol) of 2',3'-O-isopropylidene-5-fluorouridine in anhydrous pyridine (30 ml) under vigorous agitation. The mixture was agitated for about 1 hour at room temperature. The solvent was removed by distillation under reduced pressure and the residue was taken up in chloroform (100 ml) and the chloroform solution was washed successively with ice water (100 ml) and a saturated aqueous solution (100 ml)of sodium hydrogen carbonate. The chloroform phase was dried with sodium sulfate, filtered and concentrated whereby 2.68 g of 5'-O-(2-bromopropionyl)-2',3'-O-isopropylidene-5-fluorouridine was obtained.

NMR (in CDCl$_3$) δ ppm: 7.45 (d, 1H, H$_6$), 5.78 (d, 1H, H$_1$'), 1.68 (d, 3H, C$\underline{H}$$_3$—CH—), 1.54 (s, 3H, 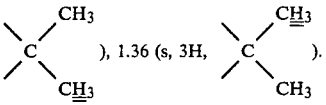), 1.36 (s, 3H, 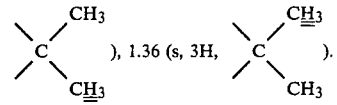).

(b) In 60 ml of acetone was dissolved 2.60 g (5.94 m-mol) of the bromo ester obtained in the above step (a), and the solution was added to an aqueous solution (20 ml) containing 3.00 g (46.1 m-mol) of sodium azide. The mixture was refluxed under heating for about 9.5 hours and the reaction liquid was concentrated under reduced pressure. The residue was distributed in 40 ml of chloroform and 40 ml of water. The aqueous phase was extracted with chloroform (40 ml×3) and the washings were combined with the previously obtained chloroform phase. The combined chloroform phase was dried with sodium sulfate, filtered and concentrated, and the residue was subjected two times to a separation-purification treatment by way of silica gel column chromatography [No. 1 column size: 3×15 cm; developing solvent: carbon tetrachloride-chloroform (2:1); No. 2 column size: 3×12 cm; developing solvent: chloroform-methanol (99:1)] whereby 2.35 g of 5'-O-(2-azidopropionyl)-2',3'-O-isopropylidene-5-fluorouridine was obtained.

NMR (in CDCl$_3$) δ ppm: 7.50 (d, 1H, H$_6$), 5.72 (d, 1H, H$_1$'), 1.55 (s, 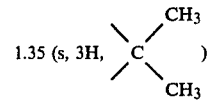), 1.5 (d, CH$_3$—CH—), 1.35 (s, 3H, 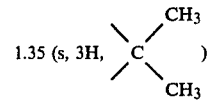)

(c) In a 90% aqueous solution (4.50 ml) of trifluoroacetic acid was dissolved 1.70 g of (4.26 m-mol) of the azido ester obtained in the above step (b), and the solution was stirred for about 30 minutes at room temperature. The reaction liquid was concentrated under reduced pressure to remove the solvents and the residue was subjected to a separation-purification treatment by way of silica gel column chromatography [silica gel 50 g; developing solvent: chloroform-methanol (98:2)] whereby 1.33 g of 5'-O-(2-azidopropionyl)-5-fluorouridine was obtained as a colorless caramel.

NMR (in CD$_2$OD) δ ppm: 7.91 (d, 1H, H$_6$), 5.92 (d, 1H, H$_1$'), 1.50 (d, 3H, CH$_3$—CH—)

IR (KBr): ν—N$^⊕$=N 2120 cm$^{-1}$

Elementary analysis: as C$_{12}$H$_{14}$N$_5$O$_7$F (M.W. 359, 27)

|  | C | H | N |
|---|---|---|---|
| Found: | 39.63% | 3.95% | 19.67% |
| Calc.: | 40.12% | 3.93% | 19.49% |

EXAMPLE 18

Preparation of 5'-O-(4-azidobutanoyl)-5-fluorouridine (a) In 15 ml of anhydrous pyridine were dissolved 1.04 g (8.06 m-mol) of 4-azidobutanoic acid and 1.00 g (3.31 m-mol) of 5-fluorouridine. To this solution was added 3.00 g (9.93 m-mol) of TPS, and the mixture was stirred overnight at room temperature. The reaction liquid was concentrated under reduced pressure and the residue was distributed in 30 ml of chloroform and 30 ml of weakly alkaline water (the pH value was adjusted at 7-8 with solid sodium carbonate). The aqueous phase was extracted with chloroform (30 ml), and the chloroform extracts were combined, dried and filtered. The filtrate was concentrated under reduced pressure and the residue was subjected twice to a separation-purification treatment by way of silica gel column chromatography [No. 1 column size: 2.1×15 cm; developing solvents: carbon tetrachloride and chloroform-methanol (99.1); No. 2 column size: 2.1×14 cm, developing solvents: chloroform and chloroform-methanol (99:1)] whereby 0.83 g of 5'-O-(4-azidobutanoyl)-2',3'-O-isopropylidene-5-fluorouridine was obtained as a colorless caramel.

NMR (in CDCl$_3$) δ ppm: 7.41 (d, 1H, H$_6$), 5.68 (d, 1H, H$_1'$), 4.8 (m, 2H, H$_2'$ and H$_3'$), 4.31 (bs, 3H, H$_4'$ and H$_5'$), 3.32 (t, 2H, N$_3$—CH$_2$—), 2.4 (bt, 2H, —CH$_2$—CO—), 1.9 (m, 2H, —CH$_2$—CH$_2$—CH$_2$—), 1.57, 1.33

(s, s, 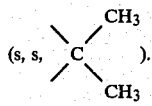 ).

(b) In 5 ml of a 90% aqueous solution of trifluoroacetic acid was dissolved 990 mg of the ester obtained in the above step (a) and the solution was stirred for 2 hours at room temperature. The reaction liquid was concentrated under reduced pressure to remove the solvent, and the residue was subjected to a separation-purification treatment by way of silica gel column chromatography [column size: 2.3×12.5 cm; developing solvents: chloroform and methanolchloroform (1:40)] whereby 560 mg of 5'-O-(4-azidobutanoyl)-5-fluorouridine was obtained as a white solid. M.P. 99°-100° (after recrystallization from isopropanol)

NMR (DMSO-d$_6$) δ ppm: 7.88 (d, 1H, H$_6$), 5.71 (dd, 1H, H$_1'$), 3.44 (bt, 2H, N$_3$—C$\underline{H}_2$—), 2.48 (—C$\underline{H}_2$—CO—), 1.84 (m, 2H, —CH$_2$—C$\underline{H}_2$—CH$_2$—).

IR (KBr): ν-N$^⊕$=N 2130 cm$^{-1}$.

Elementary analysis: as C$_{13}$H$_{16}$N$_5$O$_7$F (M.W. 373, 30)

|         | C      | H     | N      |
|---------|--------|-------|--------|
| Found:  | 42.05% | 4.26% | 18.51% |
| Calc.:  | 41.83% | 4.32% | 18.76% |

EXAMPLE 19

Preparation of 5'-O-(2-azidobutanoyl)-5-fluorouridine (a) In anhydrous pyridine (40 ml) were dissolved 3.34 g (20.0 m-mol) of 2-bromobutanoic acid and 3.00 g (9.93 m-mol) of 2',3'-O-isopropylidene-5-fluorouridine. To this solution was added 6.80 g (22.5 m-mol) of TPS, and the mixture was stirred for about 20 hours at room temperature. The reaction liquid was filtered and the filtrate was concentrated under reduced pressure. The residue was distributed in 50 ml of chloroform and 50 ml of weakly alkaline water (the pH value was adjusted at 7-8 with solid sodium carbonate), and the chloroform phase was dried with sodium sulfate, filtered and concentrated under reduced pressure. The residue was then subjected twice to a separation-purification treatment by way of silica gel column chromatography [No. 1 column size: 3.2×15 cm; developing solvents: carbon tetrachloride-chloroform (2:1) and chloroform; No. 2 column size: 3.2×12 cm; developing solvents: carbon tetrachloride-chloroform (2:1) and methanol-chloroform (1:99)] whereby 3.58 g of 5'-O-(2-bromobutanoyl)-2',3'-O-isopropylidene-5-fluorouridine was obtained as a colorless caramel.

NMR (CDCl$_3$) δ ppm: 7.51 (d, 1H, H$_6$), 5.77 (d, 1H, H$_1'$), 4.9 (m, 2H, H$_2'$, H$_3'$), 4.42 (bs, H$_4'$, H$_5'$), 4.28 ( 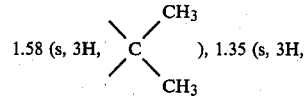 CH—Br), 2.03 (bq, 2H, —CH$_2$—), 1.58 (s, 3H, 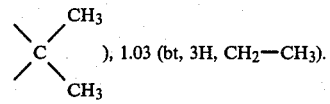 ), 1.35 (s, 3H, ), 1.03 (bt, 3H, CH$_2$—CH$_3$).

(b) In 50 ml of acetone was dissolved 2.84 g (5.25 m-mol) of the ester obtained in the above step (a). To this solution was added an aqueous solution (25 ml) containing 3.41 g (52.5 m-mol) of sodium azide, and the mixture was refluxed under heating for about 25 hours. The reaction liquid was concentrated under reduced pressure and the residue was distributed in 40 ml of chloroform and 40 ml of water. The aqueous phase was extracted with additional chloroform (40 ml×3) and the extracts were combined with the previously obtained chloroform phase. The combined chloroform phase was dried with sodium sulfate, filtered and concentrated whereby 2.08 g of 5'-O-(2-azidobutanoyl)-2',3'-O-isopropylidene-5-fluorouridine was obtained.

NMR (in CDCl$_3$) δ ppm: 7.41 (d, 1H, H$_6$), 5.65 (d, 1H, H$_1'$), 5.9 (m, H$_2'$, H$_3'$), 4.42 (bs, H$_4'$, H$_5'$), 3.82 (bt, 1H, N$_3$—CH—), 1.86 (bq, 2H, CH$_3$—CH$_2$—), 1.57 (s) and 1.36 (s) (6H, 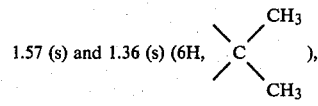 ), 1.02 (bt, 3H, —CH$_2$—CH$_3$).

(c) In chloroform (10 ml) and a 90% aqueous solution (10 ml) of trifluoroacetic acid was dissolved 2.08 g of the azido ester obtained in the above step (b), and the mixture was stirred for 30 minutes at room temperature. The reaction liquid was concentrated under reduced pressure to remove the solvent and the residue was then subjected to a separation-purification treatment by way of silica gel column chromatography [silica gel 50 g; developing solvents: chloroform and methanol-chloroform (3:97)] whereby 1.35 g of 5'-O-(2-azidobutanoyl)-5-fluorouridine was obtained as a colorless caramel which, after recrystallization from isopropanol, gave 760 mg of a crystalline substance having a melting point of 112°–114° C.

NMR (in CD$_3$OD-CDCl$_3$ in a ratio of 1:2) δ ppm: 7.74 (d, 1H, H$_6$), 5.86 (bs, 1H, H$_1'$), 4.00 (bt, —C$\underline{H}$—N$_3$), 1.90 (bq, 2H, C$\underline{H}_2$—CH$_3$), 1.05 (bt, 3H, —CH$_2$—C$\underline{H}_3$).

IR (KBr) ν-N$^\oplus$≡N: 2120 cm$^{-1}$.

Elementary analysis: as C$_{13}$H$_{16}$N$_5$O$_7$F (M.W. 373, 30)

|  | C | H | N |
|---|---|---|---|
| Found: | 41.74% | 4.41% | 18.68% |
| Calc.: | 41.83% | 4.32% | 18.76% |

EXAMPLE 20

Preparation of 5'-O-(2-azidopentanoyl)-5-fluorouridine (a) In anhydrous pyridine (20 ml) were dissolved 2.84 g (19.9 m-mol) of 2-azidopentanoic acid and 3.00 g (9.90 m-mol) of 2',3'-O-isopropylidene-5-fluorouridine. To this solution was added 6.00 g (19.8 m-mol) of TPS, and the mixture was stirred for 1.5 hours at room temperature. The reaction liquid was concentrated under reduced pressure and the residue was distributed in 100 ml of chloroform and 50 ml of a 5% aqueous solution of sodium hydrogen carbonate. The chloroform phase was dried with sodium sulfate, filtered and concentrated under reduced pressure and the residue was subjected twice to a separation-purification treatment by way of silica gel column chromatography [column size: 3×20 cm; developing solvent: methanol-chloroform (2:98)] whereby 2.70 g of 5'-O-(azidopentanoyl)-2',3'-O-isopropylidene-5-fluorouridine was obtained as a colorless caramel.

NMR (in CDCl$_3$) δ ppm: 7.35 (d, 1H, H$_6$), 5.62 (d, 1H, H$_1'$), 4.90 (m, 2H, H$_2'$, H$_3'$), 4.35 (bs, 3H, H$_4'$, H$_5'$), 3.90 (t, 1H, N—CH$_2$—), 1.57 (s, 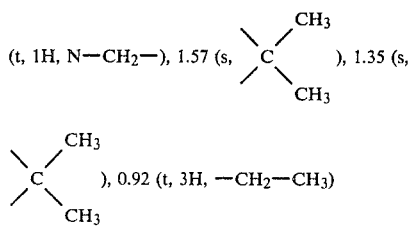), 1.35 (s, 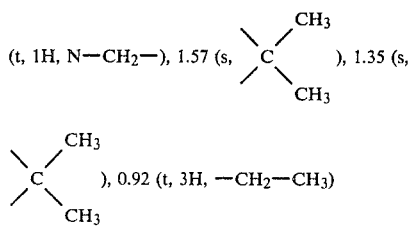), 0.92 (t, 3H, —CH$_2$—CH$_3$)

IR (neat) ν—N$^\oplus$≡N: 2100 cm$^{-1}$ (b) In 10 ml of a 90% aqueous solution of trifluoroacetic acid was dissolved 2.08 g of the ester obtained in the above step (a), and the solution was stirred for one hour at room temperature. The reaction liquid was concentrated under reduced pressure and the resultant crude crystals were recrystallized from isopropanol to afford 920 mg of crystalline 5'-O-(2-azidopentanoyl)-5-fluorouridine with a melting point of 130°–133° C.

NMR (in CD$_3$OD) δ ppm: 7.75 (d, 1H, H$_6$), 5.80 (bs, 1H, H$_1'$), 4.45 (bs, 2H, H$_2'$, H$_3'$), 4.12 (bs, 4H, H$_4'$, H$_5'$, N$_3$—C$\underline{H}$—), 1.70 (m, 4H, —CH$_2$—CH$_2$—), 0.95 (t, 3H, —CH$_2$—CH$_3$)

IR (CHCl$_3$) ν—N$^\oplus$≡N: 2100 cm$^{-1}$

Elementary analysis: as C$_{14}$H$_{18}$N$_5$O$_7$F (M.W. 387, 33)

|  | C | H | N |
|---|---|---|---|
| Found: | 43.21% | 4.62% | 17.87% |
| Calc.: | 43.41% | 4.65% | 18.09% |

EXAMPLE 21

Preparation of 5'-O-(5-azidopentanoyl)-5-fluorouridine (a) In 10 ml of anhydrous pyridine were dissolved 1.57 g (11.0 m-mol) of 5-azidopentanoic acid and 1.66 g (5.5 m-mol) of 2',3'-O-isopropylidene-5-fluorouridine. To this solution was added 3.32 g (11.0 m-mol) of TPS, and the mixture was stirred for 17 hours at room temperature. The reaction liquid was concentrated under reduced pressure and the residue was distributed in 100 ml of chloroform and 50 ml of a 5% aqueous solution of sodium hydrogen carbonate. The chloroform phase was dried with sodium sulfate, filtered and concentrated under reduced pressure and the residue was then subjected twice to a separation-purification treatment by way of silica gel column chromatography [column size: 3×20 cm; developing solvent: methanol-chloroform (1:99)] whereby 1.43 g of 5'-O-(5-azidopentanoyl)-2',3'-O-isopropylidene-5-fluorouridine was obtained as a colorless caramel.

NMR (in CDCl$_3$) δ ppm: 7.45 (d, 1H, H$_6$), 5.75 (bs, 1H, H$_1'$), 4.9 (m, 2H, H$_2'$, H$_3'$), 4.35 (bs, 3H, H$_4'$, H$_5'$), 3.30 (t, 2H, N$_3$—CH$_2$—), 2.40 (t, 2H, —CH$_2$—CO—),

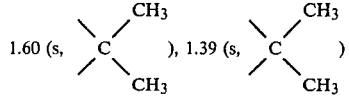

(b) In 6 ml of a 90% aqueous solution of trifluoroacetic acid was dissolved 1.2 g of the ester obtained in the above step (a), and the mixture was stirred for one hour at room temperature. The reaction liquid was concentrated under reduced pressure and the residue was subjected to a separation-purification treatment by way of silica gel column chromatography [column size: 2×15 cm; developing solvent: methanol-chloroform (5:95)] whereby 0.89 g of 5'-O-(5-azidopentanoyl)-5-fluorouridine was obtained as a colorless caramel.

NMR [in DMSO-d$_6$ and CDCl$_3$ (1:9)] δ ppm: 7.82 (d, 1H, H$_6$), 5.39 (bs, 1H, H$_1'$), 3.35 (bt, 2H, N$_3$—CH$_2$—), 2.45 (—CH$_2$—CO—), 1.70 (m, 4H, —CH$_2$—CH$_2$—).

IR (CHCl$_3$) ν—N$^\oplus$≡N: 2100 cm$^{-1}$

Elementary analysis: as C$_{14}$H$_{18}$N$_5$O$_7$F (M.W. 387, 33)

|  | C | H | N |
|---|---|---|---|
| Found: | 43.31% | 4.75% | 17.97% |
| Calc.: | 43.41% | 4.65% | 18.09% |

EXAMPLE 22

Preparation of 5'-O-(2-azidodecanoyl)-5-fluorouridine (a) In 14 ml of anhydrous pyridine were dissolved 2.8 g (13.25 m-mol) of 2-azidodecanoic acid and 2.0 g (6.62 m-mol) of 2',3'-O-isopropylidene-5-fluorouridine. To this solution was added 4.0 g (13.25 m-mol) of TPS, and the mixture was stirred for 5 hours at room temperature. The reaction liquid was concentrated under reduced pressure and the residue was subjected to silica gel column chromatography (column size: 3×35 cm; developing solvent: chloroform containing 0→5% methanol) to separate a fraction containing 5'-O-(2-azidodecanoyl)-2',3'-O-isopropylidene-5-fluorouridine. The fraction was concentrated under reduced pressure and the residue was distributed in 300 ml of benzene and 100 ml of a 5% aqueous solution of sodium hydrogen carbonate. The benzene phase was dried with sodium sulfate, filtered and concentrated under reduced pressure and the residue was subjected to silica gel column chromatography [column size: 3×25 cm; developing solvents: chloroform-carbon tetrachloride (1:1) and chloroform] whereby 3.09 g of 5'-O-(2-azidodecanoyl)-2',3'-O-isopropylidene-5-fluorouridine was obtained as a light yellow caramel.

NMR (in CDCl$_3$) δ ppm: 7.45 (d, 1H, H$_6$), 5.70 (d, 1H, H$_1'$), 3.90 (t, 1H, —C$\underline{H}$—N$_3$), 1.57 (s) and 1.35 (s) (6H, 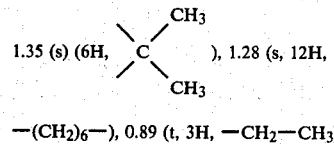 ), 1.28 (s, 12H, —(CH$_2$)$_6$—), 0.89 (t, 3H, —CH$_2$—CH$_3$).

(b) In 15 ml of a 90% aqueous solution of trifluoroacetic acid was dissolved 3.09 g of the ester obtained in the step (a), and the mixture was stirred for one hour at room temperature. The reaction liquid was concentrated under reduced pressure and the resultant crude crystals were recrystallized from isopropanol whereby 1.17 g of crystalline 5'-O-(2-azidodecanoyl)-5-fluorouridine having a melting point of 122°–125° C. was obtained.

NMR (in CD$_3$OD) δ ppm: 7.84 (d, 1H, H$_6$), 5.85 (bs, 1H, H$_1'$), 1.30 (bs, 12H,—(C$\underline{H}$$_2$)$_6$—), 0.89 (t, 3H, —CH$_2$C$\underline{H}$$_3$).

IR (KBr) ν-N⊕=N: 2120cm$^{-1}$.

Elementary analysis: as C$_{19}$H$_{23}$N$_5$O$_7$F (M.W. 457, 46)

|  | C | H | N |
|---|---|---|---|
| Found: | 49.89% | 6.23% | 15.48% |
| Calc.: | 49.89% | 6.17% | 15.31% |

EXAMPLE 23

Preparation of 5'-O-(12-azidododecanoyl)-5-fluorouridine (a) In 30 ml of anhydrous pyridine were dissolved 1.80 g (7.47 m-mol) of 12-azidododecanoic acid and 1.60 g (5.30 m-mol) of 2',3'-O-isopropylidene-5-fluorouridine. To this solution was added 4.3 g (14.2 m-mol) of TPS, and the mixture was stirred for about 18 hours at room temperature. The reaction liquid was concentrated under reduced pressure to remove the solvent and the residue was distributed in 200 ml of chloroform and 200 ml of weakly alkaline water (the pH value was adjusted at 7–8 by addition of solid sodium carbonate). The chloroform phase combined with an extract obtained by extracting the aqueous phase with chloroform (100 ml×2) was dried with sodium sulfate, filtered and concentrated under reduced pressure, and the residue was then subjected to a separation-purification treatment by way of silica gel column chromatography [column size: 3.2×22 cm; developing solvents: carbon tetrachloride and carbon tetrachloride-chloroform (3:1)] whereby 2.19 g of 5'-O-(12-azidododecanoyl)-2',3'-O-isopropylidene-5-fluorouridine was obtained as a syrupy compound.

NMR (in CDCl$_3$) δ ppm: 7.50 (d, 1H, H$_6$),
5.78 (d, 1H, H$_1'$), 3.25 (bt, 2H, N$_3$—C$\underline{H}$$_2$—),
2.35 (bt, 2H, —C$\underline{H}$$_2$—CO—),
1.57 (s) and 1.35 (s)
( 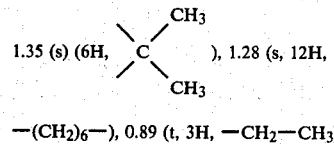 ), 1.3 (bs, —CH$_2$—(C$\underline{H}$$_2$)$_9$—CH$_2$—)

(b) In 10 ml of a 90 aqueous solution of trifluoroacetic acid was dissolved 1.02 g (1.94 m-mol) of the ester obtained in the above step (a), and the solution was stirred for 2.5 hours at room temperature. The reaction liquid was concentrated under the reduced pressure and the residue was subjected to a separation-purification treatment by way of silica gel column chromatography [column size: 3×9 cm; developing solvents: chloroform and methanol-chloroform (3:97)] whereby 0.79 g of 5'-O-(12-azidododecanoyl)-5-fluorouridine was obtained as a colorless caramel.

NMR (in CDHD 3OD) δ ppm: 7.88 (d, 1H, H$_6$), 5.82 (bs, 1H, H$_1'$), about 3.3 (N$_3$—C$\underline{H}$$_2$—), 2.41 (bt, 2H, —C$\underline{H}$$_2$—CO—), 1.4 (bs, 18H, —CH$_2$—(C$\underline{H}$$_2$)$_9$—CH$_2$—)

IR (KBr) νN⊕=N: 2100 cm$^{-1}$.

Elementary analysis: as C$_{21}$H$_{32}$N$_5$O$_7$F (M.W. 485, 51)

|  | C | H | N |
|---|---|---|---|
| Found: | 52.14% | 6.64% | 14.20% |
| Calc.: | 51.95% | 6.64% | 14.43% |

EXAMPLE 24

Preparation of 5'-O-(5-morpholinopentanoyl)-5-fluorouridine

To a solution of 2.96 g (13.2 m-mol) of 5-morpholinopentanoic acid hydrochloride in pyridine (30 ml) was added 4.2 g (13.9 m-mol) of TPS, and the mixture was stirred for 15 minutes at room temperature. To this solution was added 2.00 g (6.62 m-mol) of 2',3'-O-isopropylidene-5-fluorouridine, and the mixture was stirred for 18 hours at room temperature. The reaction liquid was concentrated under reduced pressure and the residue was distributed in chloroform (50 ml) and an 8% aqueous solution of potassium carbonate (50 ml). The aqueous phase was extracted with chloroform (50 ml ×5) and the extracts were combined with the chloroform phase previously obtained. The chloroform phase was dried with $Na_2SO_4$ and concentrated and the residue was subjected to a separation-purification treatment by way of silica gel column chromatography (column size: 5×8 cm, developing solvents: chloroform and chloroform containing 2% methanol) whereby 1.17 g of 5′-O-(5-morpholinopentanoyl)-2′,3′-O-isopropylidene-5-fluorouridine was obtained.

NMR (in $CDCl_3$) δ ppm: 7.48 (d, 1H, $H_6$),
5.73 (bs, 1H, $H'_1$), 3.7 (m, 4H, —O—$CH_2$—)
2.45 (m, 8H, —CO—$CH_2$—, $$\begin{array}{c}-CH_2\\ \diagdown \\ \diagup \\ -CH_2\end{array} N-CH_2-),\ 1.56,\ 1.35$$

(s, s, m, 10H, 
$$\begin{array}{c}\diagdown\ \diagup CH_3\\ C\\ \diagup\ \diagdown CH_3\\ -CH_2-CH_2-\end{array})$$

In a 90% aqueous solution (10 ml) of trifluoroacetic acid was dissolved 1.00 g (2.12 m-mol) of the ester obtained in the above treatment, and the solution was allowed to stand for 30 minutes at room temperature. The reaction liquid was concentrated under reduced pressure and the residue was distributed in pyridine-chloroform (1:1, 50 ml) and a 3% aqueous solution (50 ml) of potassium carbonate. The aqueous phase was extracted with pyridine-chloroform (1:1, 50 ml×2) and the organic phases were combined, dried and concentrated. The residue was subjected to a separation-purification treatment by way of silica gel column chromatography (column size: 3×15 cm; developing solvents: chloroform and chloroform containing 3% methanol) whereby 0.51 g of 5′-O-(5-morpholinopentanoyl)-5-fluorouridine was obtained as a colorless caramel.

NMR (in $CD_3OD$) δ ppm: 7.85 (d, 1H, $H_6$),
5.81 (bs, 1H, $H'_1$), 3.7 (m, 4H, —$CH_2$—O—$CH_2$—), $$2.45\ (m,\ 8H,\ -CH_2-N\begin{array}{c}\diagup CH_2-\\ \diagdown CH_2-\end{array},$$

—$CH_2$—CO—),
1.65 (m, 4H, —$CH_2$—$CH_2$—).

Elementary analysis: as $C_{12}H_{26}N_3O_8F$ (M.W. 431, 42)

| | C | H | N |
|---|---|---|---|
| Found: | 47.23% | 6.38% | 9.49% |
| Calc.: | 47.16% | 6.38% | 9.18% |

EXAMPLE 25

Preparation of 5′-O-[N-(2,3-dihydroxypropoxyacetyl)alanyl]-2′-deoxy-5-fluorouridine To a solution of 5.10 g (14.53 m-mol) of N-[2,3-O-isopropylidenepropoxyacetyl]alanine benzyl ester in isopropyl alcohol (40 ml) was added 700 mg of 10% palladium-carbon, and the mixture was stirred for 2 hours in a stream of hydrogen at room temperature. The reaction mixture was filtered and the filtrate was concentrated under reduced pressure. The resultant residue was subjected several times to an azeotropic distillation with pyridine under reduced pressure and then dissolved in pyridine (40 ml). To this solution was added 4.37 g (14.5 m-mol) of TPS, and the mixture was allowed to stand for 30 minutes at room temperature. The mixture was then combined with 3.00 g (12.18 m-mol) of 2′-deoxy-5-fluorouridine which had been subjected to an azeotropic distillation with pyridine for dehydration. The combined reaction liquid was allowed to stand for 19 hours at room temperature and concentrated under reduced pressure, and the resultant oily substance was distributed in chloroform (100 ml) and a 3% aqueous solution of potassium carbonate (70 ml). The aqueous phase was extracted with chloroform (80 ml×2) and the extracts were combined with the chloroform phase previously obtained. The chloroform phase was dried with $Na_2SO_4$, filtered and the filtrate was concentrated under reduced pressure. The residue was subjected to a separation-purification treatment by way of silica gel column chromatography (column size: 5×17 cm; developing solvents: chloroform and chloroform containing 3% methanol) whereby 2.26 g of 5′-O-[N-(2,3-O-isopropylidenepropoxyacetyl)-alanyl]-2′-deoxy-5-fluorouridine was obtained.

NMR (in $CD_3OD$) δ ppm: 7.80 (d) and 7.73 (d) (1H, $H_6$), 6.22 (bt, 1H, $H'_1$), 4.06 (s, —CO—$CH_2$—), 2.3 (m, 2H, $H'_2$), 1.47 (d, —$CH_3$),
1.42 (s) and 1.35(s) (s, 
$$\begin{array}{c}\diagdown\ \diagup CH_3\\ C\\ \diagup\ \diagdown CH_3\end{array})$$

In a 90% aqueous solution (5 ml) of trifluoroacetic acid was dissolved 2.26 g (4.62 m-mol) of the resultant ester, and the solution was allowed to stand for 5 minutes. The reaction liquid was concentrated under reduced pressure and the residue was subjected to a separation-purification treatment by way of silica gel column chromatography (column size: 3×7 cm; developing solvents: chloroform and chloroform containing 4% methanol) whereby 1.30 g of 5′-O-[N-(2,3-O-dihydroxypropoxyacetyl)alanyl]-2′-deoxy-5-fluorouridine was obtained as a colorless foam.

NMR (in $CD_3OD$) δ ppm: 7.80 (d) and 7.78 (d) (1H, $H_6$), 6.20 (bt, 1H, $H'_1$), 4.01 (s, —$CH_2$—CO—), 2.3 (m, 2H, $H'_2$), 1.45 (d, 3H, $CH_3$—$\overset{|}{CH}$—)

Elementary analysis: as $C_{17}H_{24}N_3O_{10}F$ (M.W. 449, 39)

| | C | H | N |
|---|---|---|---|
| Found: | 43.61% | 5.52% | 9.02% |
| Calc.: | 43.69% | 5.61% | 8.99% |

EXAMPLE 26

Preparation of 5′-O-(N-benzyloxycarbonylvalyl)-2′-deoxy-5-fluorouridine

In pyridine (20 ml) was dissolved 2.00 g (8.12 m-mol) of 2′-deoxy-5-fluorouridine, and the solution was cooled to −10° C. To this solution was added a solution of 2.05 g (8.16 m-mol) of N-benzyloxycarbonylvaline and 2.45 g (8.11 m-mol) of TPS in pyridine (20 ml), and the mixture was allowed to stand for 2 days under cooling (about 5° C.). The solvent was distilled off under reduced pressure from the reaction mixture and the residue was subjected twice to silica gel column chromatography [column size: 3.0×10 cm; developing solvent: CHCl₃-CH₃OH (98:2)] under the same operation conditions whereby 1.70 g (yield: 43.7%) of 5'-O-(N-benzyloxycarbonylvalyl)-2'-deoxy-5-fluorouridine was obtained as amorphous powders.

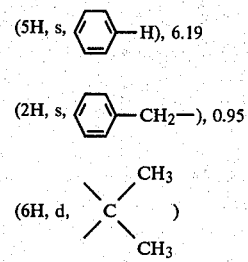

NMR (in CD₃OD) δ ppm: 7.68 (1H, d, H₆), 7.30 (5H, s, ⟨⟩—H), 6.19 (2H, s, ⟨⟩—CH₂—), 0.95 (6H, d, C(CH₃)(CH₃))

| Elementary analysis: | as C₂₂H₂₆N₃O₈F (M.W. 479, 46) | | |
|---|---|---|---|
| | C | H | N |
| Found: | 55.37% | 5.39% | 8.85% |
| Calc.: | 55.11% | 5.47% | 8.76% |

EXAMPLE 27

Preparation of 5'-O-(valyl)-2'-deoxy-5-fluorouridine

To a solution of 1.70 g (3.55 m-mol) of 5'-O-(N-benzyloxycarbonylvalyl)-2'-deoxy-5-fluorouridine obtained in Example 26 in 50 ml of isopropyl alcohol were added 10% palladium-carbon (750 mg) and a solution of 16.0% hydrogen chloride-isopropyl alcohol (810 mg). The mixture was stirred for 3.5 hours in a stream of hydrogen under normal pressure at ordinary temperature. The catalyst was filtered off and the solvent was distilled off under reduced pressure from the reaction mixture and the residue was dissolved in isopropyl alcohol (5 ml). A small amount of ether was added to this solution and the resultant white precipitate was collected by filtration in a stream of dry nitrogen whereby 1.14 g (yield: 84.1%) of 5'-O-(valyl)-2'-deoxy-5-fluorouridine hydrochloride was obtained.

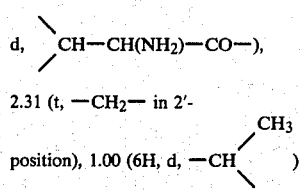

NMR (CD₃OD) δ ppm: 7.83 (2H, d, H₆), 6.20 (1H, t, H'₁), 3.57 (1H, d, CH—CH(NH₂)—CO—), 2.31 (t, —CH₂— in 2'-position), 1.00 (6H, d, —CH(CH₃)(CH₃))

| Elementary analysis: | as C₁₄H₂₀N₃O₆F · HCl (M.W. 381, 79) | | |
|---|---|---|---|
| | C | H | N |
| Found: | 42.17% | 6.25% | 9.95% |
| Calc.: | 41.87% | 6.25% | 10.46% |

EXAMPLE 28

Preparation of 5'-O-(2-morpholinopropionyl)-2'-deoxy-5-fluorouridine

In pyridine (100 ml) was dissolved 1.5 g (6.09 m-mol) of 2'-deoxy-5-fluorouridine, and the solution was cooled at −40° C. A solution of 1.60 g (9.33 m-mol) of 2-bromopropionyl chloride in dichloromethane (20 ml) was added dropwise to the above solution. Isopropyl alcohol (2 ml) was then added to the reaction liquid and the mixture was concentrated under reduced pressure. The residue was subjected to a separation-purification treatment by way of silica gel column chromatography (column size: 5×10 cm; developing solvent: chloroform containing 1→4% methanol) whereby 1.2 g (51.7%) of 5'-O-(2-bromopropionyl)-2'-deoxy-5-fluorouridine was obtained.

NMR (in CD₃OD) δ ppm:
1.70 (3H, d, CH₃CH—),
2.30 (2H, m, H'₂), 6.25
(1H, t, H'₁), 7.78 (1H, d, C₆—H)

In dioxane (20 ml) was dissolved 0.97 g (2.55 m-mol) of the ester obtained in the above treatment. To this solution was added 0.89 g (10.18 m-mol) of morpholine, and the mixture was refluxed under heating for 3 hours. After cooling the reaction liquid, the precipitate formed was filtered off and the filtrate was concentrated under reduced pressure. The residue thus obtained was then subjected to a separation-purification treatment by way of silica gel column chromatography (column size: 5×10 cm; developing solvent: chloroform containing 1→4% methanol) whereby 0.80 g (yield: 82%) of 5'-O-(2-morpholinopropionyl)-2'-deoxy-5-fluorouridine was obtained as amorphous powders.

NMR (in CD₃OD) δ ppm:
1.35 (3H, d, CH₃CH—),
2.32 (2H, t, H'₂),
2.60 (4H, m, N—CH₂),
3.70 (4H, m, O—CH₂—),
6.27 (1H, t, H'₁), 7.85 (1H, d, C₆—H)

| Elementary analysis: | as C₁₆H₂₂N₃O₇F (M.W. 387, 37) | | |
|---|---|---|---|
| | C | H | N |
| Found: | 48.17% | 5.58% | 11.54% |
| Calc.: | 49.61% | 5.72% | 10.85% |

Mass spectroanalysis: 387 (M⁺), 256, 129

EXAMPLE 29

Preparation of 1-[5-O-(N-benzyloxycarbonylalanyl)-β-D-arabinofranosyl]-5-fluorouracil In pyridine (40 ml) was dissolved 1.78 g (8.0 m-mol) of N-(benzyloxycarbonyl)-alanine. To this solution was added 2.42 g (8.01 m-mol) of TPS, and the mixture was allowed to stand for one hour at room temperature. The reaction liquid was added to 2.0 g (7.63 m-mol) of 1-(β-D-arabinofranosyl)-5-fluorouracil and the mixture was allowed to stand for 18 hours under cooling (0°–5° C.). The reaction liquid was concentrated under reduced pressure and the residue was distributed in a 3% aqueous solution (40 ml) of potassium carbonate and chloroform (50 ml). The aqueous phase was extracted with chloroform (50 ml×2) and the organic phases were combined. The organic phase was dried with Na₂SO₄ and concentrated under reduced pressure and the residue was subjected to a separation-purification treatment by way of silica gel column chromatography (column size: 5×15 cm; developing solvents: chloroform, chloroform containing 2% methanol and chloroform containing 3% methanol) whereby 2.57 g of 1-[5-O-(N-benzyloxycarbonylalanyl)-β-D-arabinofuranosyl]-5-fluorouracil was obtained as a colorless solid. M.P. 102°–8° C. (decomp. with foaming)

NMR (in CD₃OD) δ ppm: 7.75 (d, 1H, H₆), 7.29 (s, 5H, 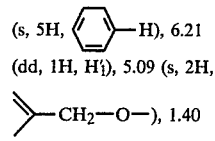—H), 6.21 (dd, 1H, H'₁), 5.09 (s, 2H, >—CH₂—O—), 1.40 (b, 3H, CH₃—CH—)

Elementary analysis: as C₂₀H₂₂N₃O₉F (M.W. 467.41)

|  | C | H | N |
|---|---|---|---|
| Found: | 50.90% | 4.42% | 9.38% |
| Calc. | 51.40% | 4.74% | 8.99% |

EXAMPLE 30

Preparation of 1-[5-O-(N-benzyloxycarbonylphenylalanyl)-β-D-arabinofuranosyl]-5-fluorouracil In pyridine (40 ml) was dissolved 2.39 g (7.99 m-mol) of N-benzyloxycarbonyl)phenylalanine. To this solution was added 2.42 g (8.01 m-mol) of TPS, and the mixture was allowed to stand for one hour at room temperature. The liquid was then added to 2.00 g (7.63 m-mol) of 1-(β-D-arabinofuranosyl)-5-fluorouracil and the mixture was allowed to stand for 18 hours under cooling (0°–5° C.). The reaction liquid was concentrated under subatmospheric pressure and the residue was distributed in a 3% aqueous solution (40 ml) of potassium carbonate and chloroform (50 ml). The aqueous phase was extracted with chlorform and the extract was combined with the chloroform phase. The combined phase was dried with Na₂SO₄ and concentrated under reduced pressure and the residue was subjected to a separation-purification treatment by way of silica gel column chromatography [column size: 5×25 cm; developing solvents: chloroform-ethyl acetate (7:3, 1.5 l) and chloroform-ethyl acetate (7:3, 1.5 l) containing 0→6% methanol in a linear gradient in concentration]-whereby 2.20 g of 1-[5-O-(N-benzyloxycarbonylphenylalanyl)-β-D-arabinofuranosyl]-5-fluorouracil was obtained as a colorless solid.

NMR (in CD₃OD) δ ppm: 7.80 (d, 1H, H₆), 7.22 (s, 5H, 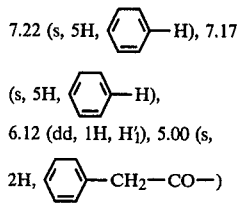—H), 7.17 (s, 5H, 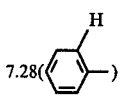—H), 6.12 (dd, 1H, H'₁), 5.00 (s, 2H, 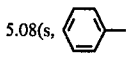—CH₂—CO—)

EXAMPLES 31–66

New nucleoside derivatives of the present invention were prepared in a similar manner to that described in any of the preceding Examples 1–28. These compounds and their NMR characteristics are shown in Table 1.

TABLE 1

| Expl. No. | Compound | Solv. | H₆ | H'₁ | Others |
|---|---|---|---|---|---|
| 31 | 5'-O-(N-benzyloxy-carbonylglycyl)-5-FUR | CD₃OD | 7.75 (d) | 5.79 (bs) | 7.28(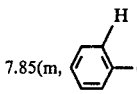—) 5.08(s, ⟨⟩—CH₂—) |
| 32 | 5'-O-(N-benzoyl-glycyl)-5-FUR | CD₃COCD₃ + CD₃OD |  | 5.83 (bs) | 7.85(m, ⟨⟩—CO—, H₆) 7.28(m, H—⟨⟩—CO—) |
| 33 | 5'-O{N-(n-pentanoylglycyl)}-5-FUR | DMSO-d₆ + D₂O | 7.85 (d) | 5.82 (bs) | 1.4(m, —CH₂—CH₂—) 0.90(bt, —CH₂—CH₃) 2.2(m-CH₂—CO—) |
| 34 | 5'-O-(N-decanoyl-glycyl)-5-FUR | DMSO-d₆ | 7.80 (d) | 5.75 (bs) | 1.25(bs, —CH₂—) 0.85(bt, —CH₂—CH₃) |

TABLE 1-continued

| Expl. No. | Compound | Solv. | H₆ | H'₁ | Others |
|---|---|---|---|---|---|
| 35 | 5'-O{N-2-benzoyl-thiopropionyl)-glycyl}-5-FUR | CD₃COCD₃ + D₂O | | 5.85 (bs) | 7.85 (m, ortho-H of C₆H₄—CO—H₆)<br>7.52 (m, meta/para-H of C₆H₄—CO—)<br>1.60 (d, —CH—CH₃) |
| 36 | 5'-O-(N-benzyloxy-carbonylalanyl)-5-FUR | CD₃OD | 7.80 (d) | 5.85 | 5.10 (s, C₆H₅—)<br>1.40 (d, —CH—CH₃) |
| 37 | 5'-O-(N-butyryl-alanyl)-5-FUR | CD₃OD | 7.88 (d) | 5.87 (bs) | 2.25 (bt, —CH₂—CO—)<br>1.65, 1.41 (m, d, —CH₂—CH₃, CH₃—CH—)<br>0.95 (t, CH₃—CH₂—) |
| 38 | 5'-O-(N-pentanoyl-alanyl)-5-FUR | CD₃OD | 7.88 (d)<br>7.85 (d) | 5.85 (bs) | 2.25 (m, —CH₂—CO—)<br>1.41 (d, m, CH₃—CH—, —CH₂—CH₂—) |
| 39 | 5'-O-(N-propionyl-methionyl)-5-FUR | CD₃OD | 7.87 (d)<br>7.85 (d) | 5.88 (bs) | 2.10 (s, —S—CH₃)<br>1.13 (t, —CH₂—CH₃) |
| 40 | 5'-O-{N-(3-carboxypropionyl)-methionyl}-5-FUR | CD₃OD | 7.87 (bd) | 5.85 (bd) | 2.58 (bs, —C(=O)—CH₂—)<br>2.08 (s, —S—CH₃) |
| 41 | 5'-O-N-(3-methoxy-carbonylpropionyl)-methionyl-5-FUR | CD₃OD | 7.85 (d)<br>7.83 (d) | 5.86 (bs) | 3.69 (s, —O—CH₃)<br>2.10 (s, —S—CH₃) |
| 42 | 5'-O-{N-(3-ethoxy-carbonylpropionyl)-methionyl}-5-FUR | CD₃OD | 7.88 (d)<br>7.85 (d) | 5.87 (bs) | 4.17 (q, —CH₂—CH₃)<br>2.10 (s, m, —S—CH₃, —CH₂—CH—)<br>1.25 (t, —CH₂—CH₃) |
| 43 | 5'-O-[N-{3-(2,2,2,-trichloroethoxy-carbonyl)-propionyl}-methionyl]-5-FUR | CD₃OD | 7.82 (d)<br>7.80 (d) | 5.85 | 4.80 (s, CCl₃·CH₂—O—)<br>2.08 (s, m, —S—CH₃, —CH₂—CH—) |
| 44 | 5'-O-(N-phenyl-acetylmethionyl)-5-FUR | CD₃OD | 7.79 (bd, 1H) | 5.80 (bs, 1H) | 2.02 (s, 3H, S—CH₃)<br>3.56 (s, 2H, C₆H₅—CH₂—)<br>7.28 (s, 5H, C₆H₅—H) |
| 45 | 5'-O-(N-ethoxy-carbonylvalyl)-5-FUR | CD₃OD | 7.86 (d) | 5.83 (bd) | 2.10 |

TABLE 1-continued

| Expl. No. | Compound | Solv. | $H_6$ | $H_1'$ | Others |
|---|---|---|---|---|---|
| 46 | 5'-O-(N-acetyl-valyl)-5-FUR | $CD_3OD$ | 7.85 (d) | 5.80 (bd) | 1.98(s, m, $CH_3CO-$, $-CH\begin{smallmatrix}CH_3\\CH_3\end{smallmatrix})$ 0.97(d, $-CH\begin{smallmatrix}CH_3\\CH_3\end{smallmatrix})$ |
| 47 | 5'-O-(N-pentanoylvalyl)-5-FUR | $CD_3OD$ | 7.86 ($d_1$) | 5.81 (bd) | 0.97(bd, $-CH\begin{smallmatrix}CH_3\\CH_3\end{smallmatrix}$, $-CH_2-CH_3$) 2.2(m, $-CH_2-CO$, $-CH\begin{smallmatrix}CH_3\\CH_3\end{smallmatrix})$ 1.5(m, $-CH_2-CH_2-$) |
| 48 | 5'-O-(N-benzyloxy-carbonylisoleucyl)-5-FUR | $CD_3OD$ | 7.78 (d) | 5.85 (bd) | 7.33(s, 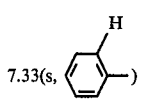) 5.08(s, 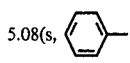$-CH_2-$) 1.25(d, $CH_3-\underset{|}{C}H-$) 0.95(bt, $CH_3-CH_2-\underset{|}{\overset{|}{C}H})$ |
| 49 | 5'-O-(N-benzyloxy-carbonylleucyl)-5-FUR | $CD_3OD$ | 7.75 (d) | 5.85 (bs) | 7.30(s, 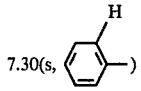) 5.08(s, 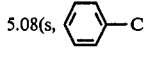$-CH_2-$) 1.6(m, $-CH_2-CH\diagup\diagdown$) 0.92(d, $-CH\begin{smallmatrix}CH_3\\CH_3\end{smallmatrix}$) |
| 50 | 5'-O-(N-propionyl-phenylalanyl)-5-FUR | $CD_3OD$ | 7.74 (d) | 5.82 (bd) 5.77 (bd) | 3.05(bd, 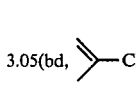$-CH_2-\underset{|}{C}H-$) 2.2 (bq, $-CH_2-CO-$) 1.05(bt, $CH_3-CH_2-$) |
| 51 | 5'-O-(N-pentanoyl-phenylalanyl)-5-FUR | $CD_3OD$ | 7.80 (d) 7.78 (d) | 5.82 (bs) 5.77 (bs) | 3.05(bd, 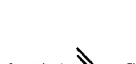$-CH_2-CH-$) 2.2 (m, $-CH_2-CO-$) 1.4 (m-$CH_2-CH_2-$) 0.9 (bt, $-CH_2-CH_3$) |

TABLE 1-continued

| Expl. No. | Compound | Solv. | $H_6$ | $H'_1$ | Others |
|---|---|---|---|---|---|
| 52 | 5'-O-(N-propionyl-tyrosyl)-5-FUR | $CD_3OD$ | 7.80 (d) 7.78 (d) | 5.85 (bs) | 7.05 (d, HO—C₆H₃(H,H)—CH₂—) 6.70 (d, HO—C₆H₃(H,H)—CH₂—) 3.00 (bd, >CH₂—CH—) 2.21 (bq, —CH₂—CO—) 1.05 (t, CH₃—CH₂—) |
| 53 | 5'-O-(N-benzyloxy-carbonyl-S-benzyl-cysteinyl)-5-FUR | $CD_3OD$ | 7.76 (bd, 1H) | 5.80 (bd, 1H) | 7.36, 7.29 (s, s, 5H, 5H, Ph—CH₂—) 5.13 (s, 2H, >CH₂—O—) 3.75 (s, 2H, >CH₂—S—) 2.80 (bd, 2H, S—CH₂—CH=) |
| 54 | 5'-O-(N-benzyloxy-carbonyltriptophyl)-5-FUR | $CD_3OD$ | | 5.64 (bs) | 7.29 (m, aromatic H, $H_6$) 5.09 (s, Ph—CH₂—O—) 3.24 (bd, indolyl—CH₂—CH—) |
| 55 | 5'-O-(N-benzyloxy-carbonylseryl)-5-FUR | $CD_3OD$ | 7.79 (b) | 5.80 (bs) | 7.30 (Ph—) 5.10 (s, >CH₂—) |
| 56 | 5'-O-morpholino-acetyl-5-FUR | $CD_3OD$ | 7.91 (d) | 5.84 (bd) | 3.7 (m, O(CH₂—)₂) 3.34 (s, N—CH₂—CO—) 2.6 (m, —N(CH₂—)₂) |
| 57 | 5'-O-(N-morpholino-propionyl)-5-FUR | $CD_3OD$ | 7.85 (d) | 6.27 (bt) | 3.7 (m, —CH₂—C—CH₂—) 2.6 (m, —CH₂—N—CH₂—) 2.32 (m, $H'_2$) 1.35 (d, CH₃—CH=) |

TABLE 1-continued

| Expl. No. | Compound | Solv. | $H_6$ | $H'_1$ | Others |
|---|---|---|---|---|---|
| 58 | 5'-O-(N-benzyloxy-carbonylalanyl)-2'-DFUR | CD$_3$OD | 7.66 (d) | 6.19 (bt) | 7.29(s, 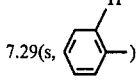) <br> 5.09(s, >—CH$_2$—O—) <br> 2.25(m, H$'_2$) <br> 1.41(d, CH$_3$—CH) |
| 59 | 5'-O-(N-lactoyl-alanyl)-2'-DFUR | CD$_3$OD | 7.82 (d) 7.79 (d) | 6.23 (bt) | 2.3(m, H$'_2$) <br> 1.43, 1.33, (d, d, CH$_3$—CH—O—, CH$_3$—CH—N—) |
| 60 | 5'-O-(N-butyryl-β-alanyl)-2'-DFUR | CD$_3$OD | 7.81 (d) | 6.22 (bt) | 3.49(bt, —NH—CH$_2$—CH$_2$—) <br> 2.15~2.6(m, —CH$_2$—CO—) <br> 1.65(m, CH$_3$—CH$_2$—) <br> 0.92(t, —CH$_2$—CH$_3$) |
| 61 | 5'-O-(N-benzyloxy-carbonylphenyl-alanyl)-2'-DFUR | CD$_3$OD | 7.65 (d) | 6.15 (bt) | 7.25(s, 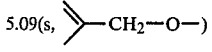) <br> 7.19(s, 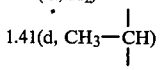) <br> 5.01(s, >—CH$_2$—O—) <br> 3.06(bd, >—CH$_2$—CH—) <br> 2.12(m, H$'_2$) |
| 62 | 5'-O-phenylalanyl-2'-DFUR-hydro-chloride | CD$_3$OD | 7.71 (d) | 6.18 (bt) | 7.30(s, 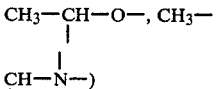) <br> 3.25( >—CH$_2$—CH—,) <br> 2.22(m, H$'_2$) |
| 63 | 5'-O-(N-propionyl-tyrosyl)-2'-DUFR | CD$_3$OD | 7.79 (d) 7.72 (d) | 6.20 (bt) | 6.98(d, 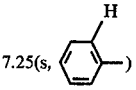—CH$_2$—) <br> 6.70(d, HO—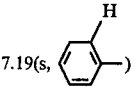—) <br> 2.83(d, >—CH$_2$—CH—) <br> 2.18(bq-CH$_2$—CH$_3$) <br> 1.07(t, —CH$_2$CH$_3$) |
| 64 | 5'-O-(N-pentanoyl-α-glutamyl)-2'- | CD$_3$COCD$_3$ -D$_2$O | 7.87 (d) | 6.25 (bt) | 2.35(m, —CH$_2$—, —CH$_2$CO—) |

TABLE 1-continued

| Expl. No. | Compound | Solv. | $H_6$ | $H'_1$ | Others |
|---|---|---|---|---|---|
| | DFUR | | 7.83 (d) | | 1.50(m, $-CH_2CH_2-$) 0.90(bt, 3H, $-CH_2CH_3$) |
| 65 | 5'-O-($N^\alpha$-butyryl-lysyl)-2'-DFUR | $CD_3OD$ | 7.90 (d) 7.82 (d) | 6.25 (bt) | 3.03(m, $-CH_2-NH$) 2.30(m, $-CH_2-CO-$, $H'_2$) 1.75(m, $-CH_2-CH_2-$) 0.97(bt, $-CH_2-CH_3$) |
| 66 | 5'-O-($N^\omega$-benzyloxy-carbonyl-$N^\alpha$-butyryl-lysyl)-2'-DFUR | $CD_3OD$ | 7.78 (d) 7.82 (d) | 6.21 (bt) | 7.30(s, 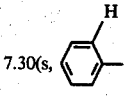) 5.04(s, $>-CH_2-O$) 3.10(m, $-CH_2-NH-$) 2.30(m, $-CH_2-CO-$, $H'_2$) 1.60(m, $-CH_2-CH_2-$) 0.93(bt, $-CH_2-CH_3$) |

The new nucleoside derivatives of the present invention were examined according to the procedure set forth hereunder to determine their anti-tumor activity in terms of Percent Increase in Life Span (ILS %) which is now widely adopted as an index for the evaluation of anti-tumor activity. A result of the examination is shown in Table 2.

[Procedure for the measurement of anti-tumor activity]

Using a group consisting of six $CDF_1$ male mice, $1 \times 10^5$ tumor cells of the lymphatic leukemia L-1210 (NIH strain) were inoculated intraperitoneally to the individual mice. On the first, fifth and ninth days from the inoculation of the tumor cells, the six mice were forced to receive, once a day, introperitoneal injection (i.p.) or oral administration (p.o.) of a suspension of Tween 80 in physiological saline containing a test compound in an amount shown in Table 2. ILS % was calculated according to the following equation in relation with the survival days of a control group of the mice not treated with the test compound:

$$ILS \% = (T-C/C) \times 100$$

wherein T stands for an average of the number of survival days of the group of mice treated with the test compound and C for an average of the number of survival days of the control group of mice treated with a placebo.

TABLE 2

| | | Compound | | | ILS (%) | | | | | | | | | | | | |
|---|---|---|---|---|---|---|---|---|---|---|---|---|---|---|---|---|---|
| | | Saturated | | | | | | | | Dose (mg/kg) body weight | | | | | | | |
| No. | Expl. No. | fatty acid moiety | Nucleoside | Administration | 0.195 | 0.39 | 0.78 | 1.56 | 3.12 | 6.25 | 12.5 | 25.0 | 50.0 | 100.0 | 200.0 | 300.0 | 400.0 |
| 1 | 1 | N-propionyl-carbamoyl-alanyl | 5-FUR | i.p. p.o. | | | | | | 24 | 50 | 76 | 108 6 | 137 19 | 57 62 | | 79 |
| 2 | 2 | N-butyl-carbamoyl-alanyl | " | i.p. p.o. | | | | | | | 50 | 69 | 82 4 | 134 13 | 79 32 | 48 | 85 |
| 3 | 3 | N-benzyloxy-carbonyl-methionyl | " | i.p. p.o. | | | | | | 46 | 58 | 152 | 153 | 161 | 141 | 72 | |
| 4 | 4 | N-decanoyl-methionyl | " | i.p. p.o. | | | | | | 58 | 62 | 93 | 130 | 128 | 64 | | |
| 5 | 5 | N-(3-phenyl-propionyl)-methionyl | " | i.p. p.o. | | | | | | | 40 | 67 | 74 | 125 | 46 | | |
| 6 | 6 | N-pentanoyl-methionyl | " | i.p. p.o. | | | 19 | 23 | 35 | 41 | 64 | 79 | 124 12 | 165 17 | 73 | | 88 |
| 7 | 9 | N-butyryl-valyl | " | i.p. p.o. | | | | | | 7 | 23 | 51 | 70 8 | 134 50 | 82 | | 101 |
| 8 | 10 | N-propionyl-valyl | " | i.p. p.o. | | | | | | 11 | 45 | 58 | 100 13 | 101 48 | 82 | | 100.0 |
| 9 | 14 | N-benzyloxy-carbonyl-phenylalanyl | " | i.p. p.o. | | | | | | | 51 | 95 | 124 | 161 | 124 | | |
| 10 | 15 | N-pentanoyl-tyrosyl | " | i.p. p.o. | | | | | | | 48 | 72 | 75 | 124 | 149 19 | | 69 |
| 11 | 16 | Azidoacetyl | " | i.p. p.o. | | | | | 82 | 89 | 147 | 97 | 60 27 | 42 62 | 96 | | 56 |

TABLE 2-continued

| No. | Expl. No. | Saturated fatty acid moiety | Nucleoside | Administration | 0.195 | 0.39 | 0.78 | 1.56 | 3.12 | 6.25 | 12.5 | 25.0 | 50.0 | 100.0 | 200.0 | 300.0 | 400.0 |
|---|---|---|---|---|---|---|---|---|---|---|---|---|---|---|---|---|---|
| 12 | 18 | 4-Azido-butanoyl | " | i.p. | | | | | | 68 | 85 | 103 | 50 | 41 | | | |
|    |    |                   | " | p.o. | | | | | | | | | | 60 | 81 | | |
| 13 | 20 | 2-azido-pentanoyl | " | i.p. | | | | | | 65 | 119 | 161 | 50 | 22 | | | |
|    |    |                   | " | p.o. | | | | | | | | | 22 | 71 | 65 | | |
| 14 | 49 | N-benzyloxy-carbonyl-triptophanyl | " | i.p. | | | | | 31 | 33 | 52 | 62 | 77 | 94 | 137 | 90 | 64 |
|    |    |                   | " | p.o. | | | | | | | | | | | | | |
| Comparative Example 1 | | H | " | i.p. | 22 | 36 | 38 | 65 | 92 | 114 | 120 | 108 | 42 | 30 | | | |
|  | | H | " | p.o. | | | | | | 11 | 19 | 32 | 44 | 62 | 64 | | 83 |
| Comparative Example 2 | | H | 2'-DFUR | i.p. | | | | | | | | | 8 | | 27 | | 83 |
|  | | | | p.o. | | | | | | | | | | | | | |

As is evident from Table 2, the new nucleoside derivatives of the present invention exhibit a high percent increase in life span not only in intraperitoneal injection but also in oral administration as compared with the known nucleosides, i.e. the fundamental compounds of the general formula (II). Accordingly, the new nucleoside derivatives of the present invention are higher in anti-tumor activity than the fundamental compounds of the general formula (II). With respect to ILS % according to intraperitoneal injection, for example, the best result in case of the fundamental compounds was obtained by 5-fluorouridine (Comparative Example 1) showing an ILS % of 120 in a dose of 12.5 mg/kg, while the Compounds Nos. 6 and 3 (and also 9) among the new nucleoside derivatives of the present invention show ILS % of 165 (in a dose of 100 mg/kg) and 161 (in a dose of 50 mg/kg), respectively. With respect to ILS % according to oral administration, the best result in case of the fundamental compounds was obtained also by 5-fluorouridine showing an ILS % of 83 in a dose of 400 mg/kg, while the Compounds Nos. 8 and 7 of the present invention show ILS % of 100 and 101, respectively, commonly in a dose of 400 mg/kg.

A safety index roughly calculated from the result shown in Table 2 according to the following equation:

$$\text{Safety index} = \frac{\text{the dose in case of the maximum } ILS \%}{\text{the dose in case of } ILS \% \text{ of 25}}$$

was about 32 in case of 5-fluorouridine (i.p.P) and about 64 in case of the Compound No. 14 of the present invention. Further, the new nucleoside derivatives of the present invention are higher in $LD_{50}$ values than the fundamental nucleosides of the general formula (II), thus showing low toxicity.

It is understood that the preceding representative examples may be varied within the scope of the present specification, both as to reactants and reaction conditions, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A nucleoside derivative of the formula:

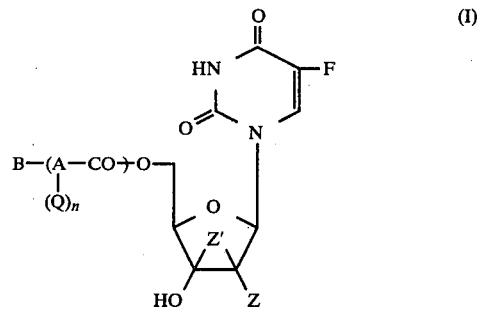

wherein (A—CO—) is a residue of a saturated straight or branched chain fatty acid having 1 to 17 carbon atoms in the alkyl moiety A thereof, B is selected from the group consisting of substituted or unsubstituted amino groups bound in the α- or ω-position, substituted or unsubstituted hydrazino groups, substituted or unsubstituted guanidino groups, diazo, azido, nitro, isocyano and 3–6 membered heterocyclic amino groups in which the ring carbon chain may be interrupted by one or more hetero atoms, with the proviso that when B is a substituted or unsubstituted amino group said amino group may be combined together with the carbon atoms in the alkyl moiety A to form a ring, Q is selected from the group consisting of hydroxyl, mercapto, alkoxy, aralkoxy, alkylmercapto, aralkylthio, substituted or unsubstituted carboxyl, substituted or unsubstituted amino, phenyl, hydroxyphenyl, sulfinyl, indolyl, imidazolyl, guanidyl and dithio connected at one end to the alkyl moiety of an amino acid, Z is H, Z' is H or OH, and n is zero or an integer of at least 1, or a physiologically acceptable salt thereof.

2. A nucleoside derivative according to claim 1, wherein the grouping

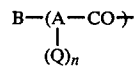

is a residue of an amino acid.

3. A nucleoside derivative according to claim 2, wherein the amino acid is a naturally occurring amino acid.

4. A nucleoside derivative according to claim 3, wherein said amino acid is derived from the protein of a living organism.

5. A nucleoside derivative according to claim 1, wherein the grouping

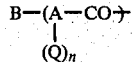

is a residue of an N-acylated amino acid.

6. A nucleoside derivative according to claim 1, wherein the grouping

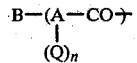

is a residue of an azido fatty acid.

7. A nucleoside derivative according to claim 1, wherein the grouping $$B-(A-CO)_{\overline{\phantom{x}}} \atop (Q)_n$$

is a residue of a fatty acid containing a nitrogen-containing heterocyclic group.

* * * * *